US007126040B2

(12) United States Patent
Prolla et al.

(10) Patent No.: US 7,126,040 B2
(45) Date of Patent: Oct. 24, 2006

(54) MOUSE MODEL FOR AGING

(75) Inventors: Tomas A. Prolla, Madison, WI (US); Gregory C. Kujoth, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/119,099

(22) Filed: Apr. 29, 2005

(65) Prior Publication Data
US 2006/0212954 A1    Sep. 21, 2006

Related U.S. Application Data

(60) Provisional application No. 60/663,930, filed on Mar. 21, 2005.

(51) Int. Cl.
*A01K 67/27* (2006.01)
*G01N 33/00* (2006.01)

(52) U.S. Cl. ............................................. 800/18; 800/3
(58) Field of Classification Search .................. 800/18, 800/3
See application file for complete search history.

(56) References Cited

OTHER PUBLICATIONS

Kirkwood T, Understanding the odd science of aging, 2005, Cell, vol. 120, pp. 437-447.*
Chomyn A, MtDNA mutations in aging and apoptosis, BBRC, 2003, vol. 304, pp. 519-529.*
Zhang D, Construction of transgenic mice with tissue-specific acceleration of mitochondrial DNA mutagenesis, 2000, Genomics, vol. 69, pp. 151-161.*
Bua, E. A., et al., "Calorie Restriction Limits the Generation but not the Progression of Mitochondrial Abnormalities in Aging Skeletal Muscle, " The FASEB Journal 18:582-584 (2004).
Cohen, H.Y., et al., "Calorie Restriction Promotes Mammilian Cell Survival by Inducing the SIRT1 Deacetylase." Science 305:390-392 (2004).
Corral-Debrinski, M., et al., "Mitochondrial DNA Deletions in Human Brain: Regional Variability and Increase with Advanced Age," Nat. Genet. 2:324-329 (1992).
Del Bo, R., et al., "Remarkable Infedelity of Polyermase LambdaA Associated with Mutations in POLYG1 Exonuclease Domain," Neurology 61:903-908 (2003).
Dillian, A., et al., "Rates of Behavior and Aging Specified by Mitochondrial Function During Development," Science 298:2398-2401 (2002).
Fleming, J.E., et al., "Is Cell Aging Caused by Respiration-Dependent Injury to the Mitochondrial Genome?," Gerontology 28:44-53 (1982).
Foury, F., Yeast Mitochondrial DNA Mutators with Deficient Proofreading Exonucleolytic Activity, EMBO Journal 11:2717-2726 (1992).
Khaidakov, M., et al., "Accumulation of Point Mutations in Mitochondrial DNA of Aging Mice," Mutation Research 526:1-7 (2003).

Lee, C.M., et al., "Mutliple Mitochondrial DNA Deletions Associated with Age in Skeletal Muscle of Rhesus Monkeys," J. Gerontology 48:B201-B205 (1993).
Lee, S.S., et al., "A Systematic RNAi Screen Identifies a Critical Role for Mitochondria in C. elegans Longevity, " Nat. Genetics 33:40-48 (2003).
Martin, G.M., et al., "Mice and Mitochondria," Nature 429:357-359 (2004) (page 358 missing due to publishers error).
Melov, S., et al., "Multi-organ Characterization of Mitochondrial Genomic Rearrangements in ad libitum and caloric restricted mice...," Nucleic Acids Research 25:974-982 (1997).
Michikawa, Y., et al., "Aging-Dependent Large Accumulation of Point Mutations in Human mtDNA Control Region for Replication," Science 286:774-779 (1999).
Nagy, A., et al., "Dissecting the role of N-myc in Development Using a Single Targeting Vector to Generate a Series of Alleles," Curr. Biol. 8:661-664 (1998).
Nicholson, D.W., et al., "Identification and Inhibition of the ICE/CED-3 Protease Necessary for Mammalian Apoptosis," Nature 376:37-43 (1995).
Pak, J.W., et al., "Mitochondrial DNA Mutations as a Fundamental Mechanism in Physiological Declines Associated with Aging," Aging Cell 2:1-7 (2003).
Parrinello, S., et al., "Oxygen Sensitivity Severely Limits the Replicative Lifespan of Murine Fibroblasts," Nature Cell Biology 5:741-747 (2003).
Taylor, R.W., et al., "Mitochondrial DNA Mutations in Human Colonic Crypt Stem Cells," J. Clniical Investigation 112:1351-1360 (2003).
Wallace, D.C., et al., "Sequence Analysis of cDNAs for the Human and Bovine ATP Synthase Beta subnit: Mitochondrial DNA genes Sustain Seventeen Times More Mutations," Curr. Genetics 12:81-90 (1987).
Wanagat, J., et al., "Mitochondrial DNA Deletion Mutations Colocalize with Segmental Electron Transport System Abnormalities, . . .," FASEB 15:322-332 (2001).
Wang, E., et al., "The rate of Mitochondrail Mutagenesis is Faster in Mice than Humans," Mutation Research 377:157-166 (1997).
Wang, Y., et al., "Muscle-Specific Mutations Accumulate with Aging in Critical Human mtDNA Control Sited for Replication," PNAS 98:4022-4027 (2001).
Zhang, D., et al., "Construction of Transgenic Mice with Tissue-Specific Acceleration of Mitochondrial DNA Mutagenesis," Genomics 69:151-161 (2000).
Zhang, Q.Y., et al., "Assessment of Hearing in 80 Inbred Strains of Mice by ABR Threshold Analysis," Hearing Research 130:94-107 (1999).
Aleksandra Trifunovic, et al; Premature ageing in mice expressing defective mitochodrial DNA polymerase; Nature, May 27, 2004; vol. 429, pp. 417-423; Nature Publishing Group; USA.

* cited by examiner

*Primary Examiner*—Dave Trong Nguyen
*Assistant Examiner*—David A. Montanari
(74) *Attorney, Agent, or Firm*—Quarles & Brady, LLP

(57) ABSTRACT

A mouse model for mammalian aging is disclosed. In one embodiment, the invention comprises a mouse having a genomic mutation in the exonuclease domain II (ExoII) of a mitochondrial DNA polymerase gamma (PolG) gene, wherein the mutation leads to high levels of mutations in polymerase mtDNA.

9 Claims, 15 Drawing Sheets

Mouse PolgA Gene Targeting

A

B
PolgA<sup>D257Aneo</sup> (targeted) allele

C
PolgA<sup>D257A</sup> (rearranged) allele

D

A

B

SEQUENCE LISTING

<160> NUMBER OF SEQ ID NOS: 5

<210> SEQ ID NO 1
<211> LENGTH: 4523
<212> TYPE: DNA
<213> ORGANISM: Mus musculus
<220> FEATURE:
<221> NAME/KEY: misc_feature
<222> LOCATION: (4458)..(4458)
<223> OTHER INFORMATION: n is a, c, g, or t
<220> FEATURE:
<221> NAME/KEY: misc_feature
<222> LOCATION: (4465)..(4466)
<223> OTHER INFORMATION: n is a, c, g, or t
<220> FEATURE:
<221> NAME/KEY: misc_feature
<222> LOCATION: (4472)..(4472)
<223> OTHER INFORMATION: n is a, c, g, or t
<220> FEATURE:
<221> NAME/KEY: misc_feature
<222> LOCATION: (4474)..(4474)
<223> OTHER INFORMATION: n is a, c, g, or t
<220> FEATURE:
<221> NAME/KEY: misc_feature
<222> LOCATION: (4501)..(4501)
<223> OTHER INFORMATION: n is a, c, g, or t

<400> SEQUENCE: 1
gggaagttgc ggctgctccc gagaccgcac gccaccctga ggctgcgtgg gccgcgcgcc      60
gcgacgccgc gtcgtcgccg gggctgtggg ctgccgcaga acgggaagcg cgaagcggac     120
cgaggacttg tgtgaggaag gcaggcatgg tgagacctat ttcactgaca ggagcacaga     180
gaggggacgc gtctctctct gagtctttcg gccactaaaa gcagtcaagc tggagcccaa     240
agcccggtgc cccgactcac agcgggggc tccctgcacc aaccatgagc cgcctgctct      300
ggaagaaggt ggctggcgcc aaggtcgcct cagggccagt accagcaacc gagggctggg     360
tctccagctc cgtcctcgca cccgtcccca gcgacgggcg gccgccgtcg caaatgccct     420
cctccgagaa tgggcagctg cggctcaacc ctctgctcat ccagatgttg tcgagaggcc     480
tgcacgagca gatcttcggg tgcggcgggg aaatgcccga cgaggccgcg gtgcagcgca     540
gcgtagagca cctgcagaag cacgggctct gggggcagcc ggccacgccc ttgccagacg     600
tggagctgcg cctgccccgg ctcttcgggg gcaacctgga ccagcacttc cgcctcctgg     660
cccagaagca gagcctgcct tacttggagg cggccgcctc gttattggag gcccaattgc     720
cccccgagcc caagagctgg gcttggcgg agggctggaa ccggtacggc cccgaggggg      780
aggccgaacc cgtggccatc cccgaggagc gggccctggt gttcgacgtg gaggtctgct     840
tggcagaggg aacctgcccc actttggcgg tggccatatc cccctcggcc tggtattcct     900
ggtgcagccg gcggctggtg gaagagcgtt actcttggac cagccagcta tcgccggctg     960
acctaacccc tttgggggc tccactagtg ccagcagctc caccaagcag gatgggcagg      1020
aacagttagt ggtggggcac aatgtttcct ttgaccgagc ccatatcagg gaacagtatc     1080
tgattcagga ctcccggatg cgttttctcg atactatgag catgcacatg gccatctcgg     1140
ggctgagcag cttccagcgc agcctgtgga tgggagccaa gcagggaaag caacaagacc     1200
cagcagtcca caaagcgagg gcagaagtcc ccgaggaaag ccaatggtcc agcgattcat     1260
cttgggactg gatggatatc agcagtgcca ataatcttgc agatgtgcac aacctttatg     1320 tgggggacc tcccttagag aaggagcctc gggagctgtt cgtcaaaggc agcatgaggg      1380
atatccgaga gaacttccag gatctgatgc agtactgcgc ccgtgatgtg tgggccacct     1440

-continued

```
ttgaggtttt ccagcagcag ctgccactct tcttggagag gtgtcccac ccagtgactc    1500 tggctggcat gctggagatg ggtgtgtcct acctgcctgt caaccagaac tgggagcgtt    1560
acctgacaga ggcacagaac acatatgagg agctccagcg ggacgatgaa gaagtcgttg    1620
tagtctggct aatgatgcct ggtcagttgc tctcaggaga gaggtacaaa aagacccttt    1680
ggctctggga cctagaatgg gatttgcagg agtttaagca gaaaaaggca aagaaggtga    1740
agaagccagc ctcagccagc aagttgccca tcgagggagc tgggcccttt ggggatccca    1800
tggatcagga gatcctggcc ccgcccagcg aggaggagga gcttcagcga agtgtaacag    1860
cccacaaccg gttacagcag ctgaggagca ccacggacct cctgcctaag cgaccccagc    1920
accttccagg acaccctggg tggtaccgga agctctgccc tcgactagat gaccctgcct    1980
gggctcccgg ccccagcctc ctcagcctgc aaatgcgggt cactcctaag ctcatggcac    2040
tgacctggga tggttttcct ctacactact cagactctca tggttggggc tacctagtgc    2100
ctgggcgtcg ggataatctg accgagccgc cagtgagccc cactgtagaa tccgctgcag    2160
taacctgccc ctacagagcc atcgagtcct tatacaggaa gcactgcctt gaacagggga    2220
agcagcaatt ggagccccag gaggtagacc tggctgagga gttcttactc actgacagta    2280
gtgccatgtg gcaaacggta gaagaactgg gctgcttaga cgtagaggct gaggccaaga    2340
tggagaattc agggctgagc caacctctag ttctgcctgc tgcttgtgcc cccaaatcca    2400
gccagcccac gtatcaccat ggcaacggac cttataatga tgtgaatatc cctggttgct    2460 ggttttcaa gctgcctcac aaggacggta acaactacaa tgtgggcagt ccctttgcca    2520
aagatttcct gcccaagatg gaggatggca ccctgcaggc tggcccagga ggtgccagtg    2580
ggcctcgtgc cctggaaata aataaaatga tttcttttg gaggaatgct cataaacgta    2640
tcagttccca gatggtggta tggctcccca ggtcagctct gccccgggtt gtgaccaggc    2700
acccagcttt cgatgaggaa ggccactatg gggccatcct accccaggtg gtgactgctg    2760
gcaccatcac ccgtcgagct gtggagccca cgtggctcac tgccagtaat gctcggcctg    2820
accgggtagg cagtgagttg aaagccatgg tgcaggctcc aactggctat gtccttgtgg    2880
gtgctgatgt ggactcacag gaactgtgga tcgcagctgt acttggagat gctcacttag    2940
ctgggatgca tggctgcacg gccttttggct ggatgactct gcagggcagg aagagcagag    3000
gcactgatct gcacagcaag acagctgcca ctgtgcgcat ccaccgagag catgccaaaa    3060
tcttcaacta tggccgcatc tatggggctg ggcagtcctt tgctgagcgc ctactgatgc    3120
agttcaacca caggctcaca aggcaggagg cagctgagaa ggcccagcag atgtatgcag    3180
tcacaaaagg cctgcgccgg tatcggctgt ctgcggatgg tgagtggctg gtgaaacagt    3240
tgaatcttcc tgtggacagg acagaggacg gctgggtctc cctacaagat cttcgaatga    3300
tccgaagaga agcttcaagg aagtcacgat ggaagaagtg ggaggtagcc tctgaacgag    3360
catggacagg gggcacagag tcagaaatgt ttaataagct ggagagtatt gccatgtctg    3420
atacaccacg tacccccagta ctgggctgct gcatcagcag agccttggag ccctcagttg    3480
tccagggaga gtttataacc agtcgtgtga actgggtggt acagagctct gctgtagact    3540
acttacatct catgcttgtg gccatgaagt ggctgtttga ggaatttgcc attgatgggc    3600
gcttctgcat cagcatccac gacgaggttc gctacctggt gcgtgaggag gaccgctacc    3660
gtgccgccct ggcactgcag atcaccaatc tcctgaccag gtgcatgttt gcctataagc    3720
tgggtctgaa tgatctgccc cagtcagtcg cctttttcag tgcagtagac attgaccagt    3780
```

```
                                                     -continued gcctcaggaa ggaagtgacc atggactgta aaactccttc taacccaact gggatggaaa    3840
ggagatatgg gatcccccag ggtgaagcac tggatattta ccagataatt gaactcacca    3900
aaggctcctt ggaaaaacgg aagccagcct ggaccctagc tctgtctgga ggttctgtat    3960
ttgctcctgt ggagctttat tggagcggtg caggttccta aactcaggct ttcagatgtg    4020
cttttttgca aaaggcagcc attttttctgt agcaggacct gcccaggaaa gtcctcctaa    4080
cggaaggcac aattcagtgc gttcagaacc aggacaccaa catcagtgca ggctgtgtga    4140 caagggtac tgttgggcac aaatgaagca gatgccccaa aggtcacatt aactcaggca     4200
tttcttcctc ctcttcttgg ctggttctct gtcctgctgt gtatgtgctg atgcagtgcc    4260
ctagaagggg agagtagaaa ttttgacaac cttgttctaa ggtgatggga ataaaaacaa    4320
acaccaaact cctggaacag ttgtgctttc ccgtctgctg cccaggttgt gacttagaac    4380
tccgtcctga gtagatggac gagatgctgg gagcccggag catcacagct acagacggcc    4440
tggggcacag tccgtacnga actgnncatc ancnagctag ccagattatt ttatataaat    4500
ntctaatttt tactgggaag aaa                                            4523

<210> SEQ ID NO 2
<211> LENGTH: 1238
<212> TYPE: PRT
<213> ORGANISM: Mus musculus

<400> SEQUENCE: 2

Met Ser Arg Leu Leu Trp Lys Lys Val Ala Gly Ala Lys Val Ala Ser
1               5                   10                  15

Gly Pro Val Pro Ala Thr Glu Gly Trp Val Ser Ser Val Leu Ala
                20                  25                  30

Pro Val Pro Ser Asp Gly Arg Pro Ser Gln Met Pro Ser Ser Glu
            35                  40                  45

Asn Gly Gln Leu Arg Leu Asn Pro Leu Leu Ile Gln Met Leu Ser Arg
    50                  55                  60

Gly Leu His Glu Gln Ile Phe Gly Cys Gly Gly Glu Met Pro Asp Glu
65                  70                  75                  80

Ala Ala Val Gln Arg Ser Val Glu His Leu Gln Lys His Gly Leu Trp
                85                  90                  95

Gly Gln Pro Ala Thr Pro Leu Pro Asp Val Glu Leu Arg Leu Pro Arg
            100                 105                 110

Leu Phe Gly Gly Asn Leu Asp Gln His Phe Arg Leu Leu Ala Gln Lys
        115                 120                 125

Gln Ser Leu Pro Tyr Leu Glu Ala Ala Ser Leu Leu Glu Ala Gln
    130                 135                 140

Leu Pro Pro Glu Pro Lys Ser Trp Ala Trp Ala Glu Gly Trp Asn Arg
145                 150                 155                 160

Tyr Gly Pro Glu Gly Glu Ala Glu Pro Val Ala Ile Pro Glu Glu Arg
                165                 170                 175

Ala Leu Val Phe Asp Val Glu Val Cys Leu Ala Glu Gly Thr Cys Pro
            180                 185                 190

Thr Leu Ala Val Ala Ile Ser Pro Ser Ala Trp Tyr Ser Trp Cys Ser
        195                 200                 205

Arg Arg Leu Val Glu Glu Arg Tyr Ser Trp Thr Ser Gln Leu Ser Pro
    210                 215                 220

Ala Asp Leu Thr Pro Leu Gly Gly Ser Thr Ser Ala Ser Ser Ser Thr
225                 230                 235                 240
```

-continued

```
Lys Gln Asp Gly Gln Glu Gln Leu Val Val Gly His Asn Val Ser Phe
                245                 250                 255
Asp Arg Ala His Ile Arg Glu Gln Tyr Leu Ile Gln Asp Ser Arg Met
            260                 265                 270
Arg Phe Leu Asp Thr Met Ser Met His Met Ala Ile Ser Gly Leu Ser
        275                 280                 285
Ser Phe Gln Arg Ser Leu Trp Met Gly Ala Lys Gln Gly Lys Gln Gln
    290                 295                 300
Asp Pro Ala Val His Lys Ala Arg Ala Glu Val Pro Glu Glu Ser Gln
305                 310                 315                 320
Trp Ser Ser Asp Ser Ser Trp Asp Trp Met Asp Ile Ser Ser Ala Asn
                325                 330                 335
Asn Leu Ala Asp Val His Asn Leu Tyr Val Gly Gly Pro Pro Leu Glu
            340                 345                 350
Lys Glu Pro Arg Glu Leu Phe Val Lys Gly Ser Met Arg Asp Ile Arg
        355                 360                 365
Glu Asn Phe Gln Asp Leu Met Gln Tyr Cys Ala Arg Asp Val Trp Ala
    370                 375                 380
Thr Phe Glu Val Phe Gln Gln Leu Pro Leu Phe Leu Glu Arg Cys
385                 390                 395                 400
Pro His Pro Val Thr Leu Ala Gly Met Leu Glu Met Gly Val Ser Tyr
                405                 410                 415
Leu Pro Val Asn Gln Asn Trp Glu Arg Tyr Leu Thr Glu Ala Gln Asn
            420                 425                 430
Thr Tyr Glu Glu Leu Gln Arg Asp Glu Glu Val Val Val Val Trp
        435                 440                 445
Leu Met Met Pro Gly Gln Leu Leu Ser Gly Glu Arg Tyr Lys Glu Asp
    450                 455                 460
Pro Trp Leu Trp Asp Leu Glu Trp Asp Leu Gln Glu Phe Lys Gln Lys
465                 470                 475                 480
Lys Ala Lys Lys Val Lys Lys Pro Ala Ser Ala Ser Lys Leu Pro Ile
                485                 490                 495
Glu Gly Ala Gly Pro Phe Gly Asp Pro Met Asp Gln Glu Asp Pro Gly
            500                 505                 510
Pro Pro Ser Glu Glu Glu Leu Gln Arg Ser Val Thr Ala His Asn
        515                 520                 525
Arg Leu Gln Gln Leu Arg Ser Thr Thr Asp Leu Leu Pro Lys Arg Pro
    530                 535                 540
Gln His Leu Pro Gly His Pro Gly Trp Tyr Arg Lys Leu Cys Pro Arg
545                 550                 555                 560
Leu Asp Asp Pro Ala Trp Ala Pro Gly Pro Ser Leu Leu Ser Leu Gln
                565                 570                 575
Met Arg Val Thr Pro Lys Leu Met Ala Leu Thr Trp Asp Gly Phe Pro
            580                 585                 590
Leu His Tyr Ser Asp Ser His Gly Trp Gly Tyr Leu Val Pro Gly Arg
        595                 600                 605
Arg Asp Asn Leu Thr Glu Pro Val Ser Pro Thr Val Glu Ser Ala
    610                 615                 620
Ala Val Thr Cys Pro Tyr Arg Ala Ile Glu Ser Leu Tyr Arg Lys His
625                 630                 635                 640
Cys Leu Glu Gln Gly Lys Gln Gln Leu Glu Pro Gln Glu Val Asp Leu
                645                 650                 655
Ala Glu Glu Phe Leu Leu Thr Asp Ser Ser Ala Met Trp Gln Thr Val
```

-continued

```
            660                 665                 670
Glu Glu Leu Gly Cys Leu Asp Val Glu Ala Ala Lys Met Glu Asn
        675                 680                 685
Ser Gly Leu Ser Gln Pro Leu Val Leu Pro Ala Ala Cys Ala Pro Lys
        690                 695                 700
Ser Ser Gln Pro Thr Tyr His His Gly Asn Gly Pro Tyr Asn Asp Val
705                 710                 715                 720
Asn Ile Pro Gly Cys Trp Phe Phe Lys Leu Pro His Lys Asp Gly Asn
            725                 730                 735
Asn Tyr Asn Val Gly Ser Pro Phe Ala Lys Asp Phe Leu Pro Lys Met
            740                 745                 750
Glu Asp Gly Thr Leu Gln Ala Gly Pro Gly Gly Ala Ser Gly Pro Arg
            755                 760                 765
Ala Leu Glu Ile Asn Lys Met Ile Ser Phe Trp Arg Asn Ala His Lys
            770                 775                 780
Arg Ile Ser Ser Gln Met Val Val Trp Leu Pro Arg Ser Ala Leu Pro
785                 790                 795                 800
Arg Val Val Thr Arg His Pro Ala Phe Asp Glu Glu Gly His Tyr Gly
                805                 810                 815
Ala Ile Leu Pro Gln Val Val Thr Ala Gly Thr Ile Thr Arg Arg Ala
            820                 825                 830
Val Glu Pro Thr Trp Leu Thr Ala Ser Asn Ala Arg Pro Asp Arg Val
            835                 840                 845
Gly Ser Glu Leu Lys Ala Met Val Gln Ala Pro Thr Gly Tyr Val Leu
        850                 855                 860
Val Gly Ala Asp Val Asp Ser Gln Glu Leu Trp Ile Ala Ala Val Leu
865                 870                 875                 880
Gly Asp Ala His Leu Ala Gly Met His Gly Cys Thr Ala Phe Gly Trp
                885                 890                 895
Met Thr Leu Gln Gly Arg Lys Ser Arg Gly Thr Asp Leu His Ser Lys
            900                 905                 910
Thr Ala Ala Thr Val Arg Ile His Arg Glu His Ala Lys Ile Phe Asn
        915                 920                 925
Tyr Gly Arg Ile Tyr Gly Ala Gly Gln Ser Phe Ala Glu Arg Leu Leu
        930                 935                 940
Met Gln Phe Asn His Arg Leu Thr Arg Gln Glu Ala Ala Glu Lys Ala
945                 950                 955                 960
Gln Gln Met Tyr Ala Val Thr Lys Gly Leu Arg Arg Tyr Arg Leu Ser
                965                 970                 975
Ala Asp Gly Glu Trp Leu Val Lys Gln Leu Asn Leu Pro Val Asp Arg
            980                 985                 990
Thr Glu Asp Gly Trp Val Ser Leu  Gln Asp Leu Arg Met  Ile Arg Arg
        995                 1000                 1005
Glu Ala  Ser Arg Lys Ser Arg  Trp Lys Lys Trp Glu  Val Ala Ser
        1010                 1015                 1020
Glu Arg  Ala Trp Thr Gly Gly  Thr Glu Ser Glu Met  Phe Asn Lys
        1025                 1030                 1035
Leu Glu  Ser Ile Ala Met Ser  Asp Thr Pro Arg Thr  Pro Val Leu
        1040                 1045                 1050
Gly Cys  Cys Ile Ser Arg Ala  Leu Glu Pro Ser Val  Val Gln Gly
        1055                 1060                 1065
Glu Phe  Ile Thr Ser Arg Val  Asn Trp Val Val Gln  Ser Ser Ala
        1070                 1075                 1080
```

```
Val Asp Tyr Leu His Leu Met  Leu Val Ala Met Lys  Trp Leu Phe
    1085              1090                1095

Glu Glu Phe Ala Ile Asp  Gly Arg Phe Cys Ile Ser  Ile His Asp
    1100              1105                1110

Glu Val Arg Tyr Leu Val  Arg Glu Glu Asp Arg Tyr  Arg Ala Ala
    1115              1120                1125

Leu Ala Leu Gln Ile Thr  Asn Leu Leu Thr Arg Cys  Met Phe Ala
    1130              1135                1140

Tyr Lys Leu Gly Leu Asn  Asp Leu Pro Gln Ser Val  Ala Phe Phe
    1145              1150                1155

Ser Ala Val Asp Ile Asp  Gln Cys Leu Arg Lys Glu  Val Thr Met
    1160              1165                1170

Asp Cys Lys Thr Pro Ser  Asn Pro Thr Gly Met Glu  Arg Arg Tyr
    1175              1180                1185

Gly Ile Pro Gln Gly Glu  Ala Leu Asp Ile Tyr Gln  Ile Ile Glu
    1190              1195                1200

Leu Thr Lys Gly Ser Leu  Glu Lys Arg Lys Pro Ala  Trp Thr Leu
    1205              1210                1215

Ala Leu Ser Gly Gly Ser  Val Phe Ala Pro Val Glu  Leu Tyr Trp
    1220              1225                1230

Ser Gly Ala Gly Ser
    1235

<210> SEQ ID NO 3
<211> LENGTH: 1238
<212> TYPE: PRT
<213> ORGANISM: Mus musculus
<220> FEATURE:
<221> NAME/KEY: MISC_FEATURE
<222> LOCATION: (257)..(257)
<223> OTHER INFORMATION: Mutation, Aspartic Acid to Alanine.

<400> SEQUENCE: 3

Met Ser Arg Leu Leu Trp  Lys Lys Val Ala Gly Ala  Lys Val Ala Ser
1           5                        10                       15

Gly Pro Val Pro Ala Thr  Glu Gly Trp Val Ser Ser  Val Leu Ala
            20                       25                       30

Pro Val Pro Ser Asp Gly  Arg Pro Ser Gln Met Pro  Ser Ser Glu
            35                       40                       45

Asn Gly Gln Leu Arg Leu  Asn Pro Leu Leu Ile Gln  Met Leu Ser Arg
50                       55                       60

Gly Leu His Glu Gln Ile  Phe Gly Cys Gly Gly Glu  Met Pro Asp Glu
65                       70                       75                       80

Ala Ala Val Gln Arg Ser  Val Glu His Leu Gln Lys  His Gly Leu Trp
                85                       90                       95

Gly Gln Pro Ala Thr Pro  Leu Pro Asp Val Glu Leu  Arg Leu Pro Arg
            100                      105                      110

Leu Phe Gly Gly Asn Leu  Asp Gln His Phe Arg Leu  Leu Ala Gln Lys
            115                      120                      125

Gln Ser Leu Pro Tyr Leu  Glu Ala Ala Ser Leu Leu  Glu Ala Gln
            130                      135                 140

Leu Pro Pro Glu Pro Lys  Ser Trp Ala Trp Ala Glu  Gly Trp Asn Arg
145                      150                      155                      160

Tyr Gly Pro Glu Gly Glu  Ala Glu Pro Val Ala Ile  Pro Glu Glu Arg
                165                      170                      175
```

```
Ala Leu Val Phe Asp Val Glu Val Cys Leu Ala Glu Gly Thr Cys Pro
            180                 185                 190
Thr Leu Ala Val Ala Ile Ser Pro Ser Ala Trp Tyr Ser Trp Cys Ser
        195                 200                 205
Arg Arg Leu Val Glu Arg Tyr Ser Trp Thr Ser Gln Leu Ser Pro
    210                 215                 220
Ala Asp Leu Thr Pro Leu Gly Ser Thr Ser Ala Ser Ser Ser Thr
225                 230                 235                 240
Lys Gln Asp Gly Gln Glu Gln Leu Val Val Gly His Asn Val Ser Phe
                245                 250                 255
Ala Arg Ala His Ile Arg Glu Gln Tyr Leu Ile Gln Asp Ser Arg Met
            260                 265                 270
Arg Phe Leu Asp Thr Met Ser Met His Met Ala Ile Ser Gly Leu Ser
        275                 280                 285
Ser Phe Gln Arg Ser Leu Trp Met Gly Ala Lys Gln Gly Lys Gln Gln
    290                 295                 300
Asp Pro Ala Val His Lys Ala Arg Ala Glu Val Pro Glu Glu Ser Gln
305                 310                 315                 320
Trp Ser Ser Asp Ser Ser Trp Asp Trp Met Asp Ile Ser Ser Ala Asn
                325                 330                 335
Asn Leu Ala Asp Val His Asn Leu Tyr Val Gly Gly Pro Pro Leu Glu
            340                 345                 350
Lys Glu Pro Arg Glu Leu Phe Val Lys Gly Ser Met Arg Asp Ile Arg
        355                 360                 365
Glu Asn Phe Gln Asp Leu Met Gln Tyr Cys Ala Arg Asp Val Trp Ala
    370                 375                 380
Thr Phe Glu Val Phe Gln Gln Leu Pro Leu Phe Leu Glu Arg Cys
385                 390                 395                 400
Pro His Pro Val Thr Leu Ala Gly Met Leu Glu Met Gly Val Ser Tyr
            405                 410                 415
Leu Pro Val Asn Gln Asn Trp Glu Arg Tyr Leu Thr Glu Ala Gln Asn
        420                 425                 430
Thr Tyr Glu Glu Leu Gln Arg Asp Asp Glu Val Val Val Val Trp
    435                 440                 445
Leu Met Met Pro Gly Gln Leu Leu Ser Gly Glu Arg Tyr Lys Glu Asp
450                 455                 460
Pro Trp Leu Trp Asp Leu Glu Trp Asp Leu Gln Glu Phe Lys Gln Lys
465                 470                 475                 480
Lys Ala Lys Lys Val Lys Lys Pro Ala Ser Ala Ser Lys Leu Pro Ile
                485                 490                 495
Glu Gly Ala Gly Pro Phe Gly Asp Pro Met Asp Gln Glu Asp Pro Gly
            500                 505                 510
Pro Pro Ser Glu Glu Glu Glu Leu Gln Arg Ser Val Thr Ala His Asn
        515                 520                 525
Arg Leu Gln Gln Leu Arg Ser Thr Thr Asp Leu Leu Pro Lys Arg Pro
    530                 535                 540
Gln His Leu Pro Gly His Pro Gly Trp Tyr Arg Lys Leu Cys Pro Arg
545                 550                 555                 560
Leu Asp Asp Pro Ala Trp Ala Pro Gly Pro Ser Leu Leu Ser Leu Gln
                565                 570                 575
Met Arg Val Thr Pro Lys Leu Met Ala Leu Thr Trp Asp Gly Phe Pro
            580                 585                 590
Leu His Tyr Ser Asp Ser His Gly Trp Gly Tyr Leu Val Pro Gly Arg
```

```
                    595                 600                 605
Arg Asp Asn Leu Thr Glu Pro Pro Val Ser Pro Thr Val Glu Ser Ala
    610                 615                 620

Ala Val Thr Cys Pro Tyr Arg Ala Ile Glu Ser Leu Tyr Arg Lys His
625                 630                 635                 640

Cys Leu Glu Gln Gly Lys Gln Gln Leu Glu Pro Gln Glu Val Asp Leu
                645                 650                 655

Ala Glu Glu Phe Leu Leu Thr Asp Ser Ser Ala Met Trp Gln Thr Val
                660                 665                 670

Glu Glu Leu Gly Cys Leu Asp Val Glu Ala Ala Lys Met Glu Asn
                675                 680                 685

Ser Gly Leu Ser Gln Pro Leu Val Leu Pro Ala Cys Ala Pro Lys
    690                 695                 700

Ser Ser Gln Pro Thr Tyr His His Gly Asn Gly Pro Tyr Asn Asp Val
705                 710                 715                 720

Asn Ile Pro Gly Cys Trp Phe Phe Lys Leu Pro His Lys Asp Gly Asn
                725                 730                 735

Asn Tyr Asn Val Gly Ser Pro Phe Ala Lys Asp Phe Leu Pro Lys Met
                740                 745                 750

Glu Asp Gly Thr Leu Gln Ala Gly Pro Gly Gly Ala Ser Gly Pro Arg
                755                 760                 765

Ala Leu Glu Ile Asn Lys Met Ile Ser Phe Trp Arg Asn Ala His Lys
    770                 775                 780

Arg Ile Ser Ser Gln Met Val Val Trp Leu Pro Arg Ser Ala Leu Pro
785                 790                 795                 800

Arg Val Val Thr Arg His Pro Ala Phe Asp Glu Glu Gly His Tyr Gly
                805                 810                 815

Ala Ile Leu Pro Gln Val Val Thr Ala Gly Thr Ile Thr Arg Arg Ala
                820                 825                 830

Val Glu Pro Thr Trp Leu Thr Ala Ser Asn Ala Arg Pro Asp Arg Val
                835                 840                 845

Gly Ser Glu Leu Lys Ala Met Val Gln Ala Pro Thr Gly Tyr Val Leu
    850                 855                 860

Val Gly Ala Asp Val Asp Ser Gln Glu Leu Trp Ile Ala Ala Val Leu
865                 870                 875                 880

Gly Asp Ala His Leu Ala Gly Met His Gly Cys Thr Ala Phe Gly Trp
                885                 890                 895

Met Thr Leu Gln Gly Arg Lys Ser Arg Gly Thr Asp Leu His Ser Lys
                900                 905                 910

Thr Ala Ala Thr Val Arg Ile His Arg Glu His Ala Lys Ile Phe Asn
                915                 920                 925

Tyr Gly Arg Ile Tyr Gly Ala Gly Gln Ser Phe Ala Glu Arg Leu Leu
    930                 935                 940

Met Gln Phe Asn His Arg Leu Thr Arg Gln Glu Ala Ala Glu Lys Ala
945                 950                 955                 960

Gln Gln Met Tyr Ala Val Thr Lys Gly Leu Arg Arg Tyr Arg Leu Ser
                965                 970                 975

Ala Asp Gly Glu Trp Leu Val Lys Gln Leu Asn Leu Pro Val Asp Arg
                980                 985                 990

Thr Glu Asp Gly Trp Val Ser Leu Gln Asp Leu Arg Met Ile Arg Arg
                995                 1000                1005

Glu Ala Ser Arg Lys Ser Arg Trp Lys Lys Trp Glu Val Ala Ser
    1010                1015                1020
```

```
Glu Arg Ala Trp Thr Gly Gly Thr Glu Ser Glu Met Phe Asn Lys
    1025            1030            1035

Leu Glu Ser Ile Ala Met Ser Asp Thr Pro Arg Thr Pro Val Leu
    1040            1045            1050

Gly Cys Cys Ile Ser Arg Ala Leu Glu Pro Ser Val Val Gln Gly
    1055            1060            1065

Glu Phe Ile Thr Ser Arg Val Asn Trp Val Val Gln Ser Ser Ala
    1070            1075            1080

Val Asp Tyr Leu His Leu Met Leu Val Ala Met Lys Trp Leu Phe
    1085            1090            1095

Glu Glu Phe Ala Ile Asp Gly Arg Phe Cys Ile Ser Ile His Asp
    1100            1105            1110

Glu Val Arg Tyr Leu Val Arg Glu Glu Asp Arg Tyr Arg Ala Ala
    1115            1120            1125

Leu Ala Leu Gln Ile Thr Asn Leu Leu Thr Arg Cys Met Phe Ala
    1130            1135            1140

Tyr Lys Leu Gly Leu Asn Asp Leu Pro Gln Ser Val Ala Phe Phe
    1145            1150            1155

Ser Ala Val Asp Ile Asp Gln Cys Leu Arg Lys Glu Val Thr Met
    1160            1165            1170

Asp Cys Lys Thr Pro Ser Asn Pro Thr Gly Met Glu Arg Arg Tyr
    1175            1180            1185

Gly Ile Pro Gln Gly Glu Ala Leu Asp Ile Tyr Gln Ile Ile Glu
    1190            1195            1200

Leu Thr Lys Gly Ser Leu Glu Lys Arg Lys Pro Ala Trp Thr Leu
    1205            1210            1215

Ala Leu Ser Gly Gly Ser Val Phe Ala Pro Val Glu Leu Tyr Trp
    1220            1225            1230

Ser Gly Ala Gly Ser
    1235
```

<210> SEQ ID NO 4
<211> LENGTH: 25
<212> TYPE: DNA
<213> ORGANISM: Artificial
<220> FEATURE:
<223> OTHER INFORMATION: Synthetic oligonucleotide

<400> SEQUENCE: 4
gccaactagc ctccatctca tactt          25

<210> SEQ ID NO 5
<211> LENGTH: 20
<212> TYPE: DNA
<213> ORGANISM: Artificial
<220> FEATURE:
<223> OTHER INFORMATION: Synthetic oligonucleotide

<400> SEQUENCE: 5
gggcgggttg ttggtttcac          20

MOUSE MODEL FOR AGING

CROSS-REFERENCE TO RELATED APPLICATION

This application claims priority to U.S. provisional 60/663,930, Mouse Model for Aging, Tomas Prolla, et al., filed Mar. 21, 2005, incorporated by reference herein.

STATEMENT REGARDING FEDERALLY SPONSORED RESEARCH OR DEVELOPMENT

This invention was made with United States government support awarded by NIH R01 AG021905. The United States government has certain rights in this invention.

BACKGROUND OF THE INVENTION

Mitochondria are intracellular organelles that are the main source of ATP, and play a central role in several metabolic processes including fatty acid β-oxidation, phospholipid biosynthesis, calcium signaling and reactive oxygen species (ROS) generation. Mitochondria also play a critical role in the process of apoptosis, since numerous pro-apoptotic molecules and pathological stimuli converge on these organelles leading to outer membrane permeabilization and cell death (D. R. Green and G. Kroemer, Science 305:626–9, 2004).

Because mitochondria are the main source of ROS in the cell and the organelle contains its own ~16 kbp circular DNA, a central role for mtDNA mutations in aging has been postulated (J. E. Fleming, et al., Gerontology (Basel) 28:44–53, 1982). Indeed, mtDNA has a higher mutation rate as compared to nuclear DNA (D. C. Wallace et al., Curr. Genet. 12:81–90, 1987) and mtDNA mutations have been shown to accumulate with aging in several tissues of various species (Y. Wang, et al., Proc. Natl. Acad. Sci. USA 98:40224027, 2001; S. Melov, et al., Nucleic Acids Res. 25:974–982, 1997; M. Corral-Debrinksi, et al., Nat. Genet. 2:324–329, 1992; C. M. Lee, et al., J. Gerontol. Biol. Sci. 48:B201–B205, 1993; M. Khaidakov, et al., Mutat. Res. 526:1–7, 2003), and in cells derived from aged humans (Y. Michikawa, et al., Science 286:774–779, 1999).

In agreement with a central role for mitochondria in aging, a systematic RNA interference (RNAi) screen of C. elegans for gene inactivations that increase lifespan has revealed genes important for mitochondrial function (S. S. Lee, et al., Nat. Genet. 33:4048, 2003), and inhibition of mitochondrial activity in this organism affects lifespan (A. Dillin, et al., Science 298:2398–2401, 2002).

BRIEF SUMMARY OF THE INVENTION

In the present application, we construct mice engineered to have a high mtDNA mutation rate and provide support for a causal role of apoptosis in aging due to mtDNA mutations. We also provide an improved mouse model for aging.

In one embodiment, the present invention is a transgenic mouse model for mammalian aging comprising a mouse having a genomic mutation in an exonuclease domain, preferably the exonuclease domain II (ExoII), of a mitochondrial DNA polymerase gamma (Polg) gene (SEQ ID NO: 1), wherein the mutation is capable of maintaining mitochondrial DNA polymerase activity and impairing the exonuclease domain activity. Preferably, the mutation is selected from the group consisting of a single or double base pair nucleotide substitution.

In another embodiment, the transgenic mouse has a genomic mutation in an exonuclease domain, preferably the exonuclease domain II (ExoII), of a mitochondrial DNA polymerase gamma (Polg) gene, wherein the mutation is a nucleotide change within residues 819–836, 1026–1067 or 1413–1442 of the mouse Polg gene (as numbered in NM_017462 or SEQ ID NO: 1), and wherein the mutation is capable of maintaining mitochondrial DNA polymerase replication activity and impairing the exonuclease domain activity.

Preferably, the mutation is a double base substitution resulting in a change in the coding of residue 257 from an aspartic acid (D) to an alanine (A) in the exonuclease domain II of Polg.

In a preferred version of the invention, the mouse model exhibits symptoms of accelerated or premature aging compared to a mouse not having the mutation in the exonuclease domain of the Polg gene. The aging symptoms are preferably selected from the group consisting of abnormalities in tissues of high cellular turnover, heart dysfunction, graying hair and alopecia, auditory function loss, cochlear degeneration, immune cell loss, anemia, male germ cell loss leading to lack of sperm and infertility, skeletal muscle mass loss (sarcopenia), neurodegeneration, increased presence of apoptotic markers, and loss of bone mass.

In another embodiment, the present invention is a method of screening for a potentially therapeutic agent useful for delaying the onset of aging-related symptoms. The method typically comprises the steps of: (a) providing a mouse model as described above, wherein the mouse exhibits aging-related symptoms; (b) administering the agent to the mouse model; and (c) determining whether the agent is capable of delaying the onset of aging-related symptoms in the mouse model treated with the agent compared to an untreated mouse model.

In another embodiment, the present invention is a method of screening for a potentially therapeutic agent useful for treating medical conditions comprising progressive external ophthalmoplegia, sensorimotor polyneuropathy, ataxia, Parkinson's syndrome or early menopause defined by mitochondrial DNA mutations in a POLG gene. The method typically comprises the steps of: (a) providing a mouse model as described above, wherein the mouse exhibits symptoms of progressive external ophthalmoplegia sensorimotor polyneuropathy, ataxia, Parkinson's syndrome or early menopause; (b) administering the agent to the mouse model; and (c) determining whether the agent is capable of improving symptoms for any of the medical conditions of step (a) in the mouse model treated with the agent compared to an untreated mouse model.

In another embodiment, the present invention is a method for generating a mouse model for mammalian aging, typically comprising the steps of: (a) introducing into a mouse a germline transmission of a mutation in an exonuclease domain, preferably exonuclease domain II of a mitochondrial DNA polymerase gamma (Polg) gene, wherein the mutation results in a decrease in the Polg exonuclease activity, and wherein the mutation results in the production of a PolgA$^{exo-/+}$ mouse; (b) crossbreeding the PolgA$^{exo-/+}$ mouse of step (a); and (c) generating a homozygous PolgA$^{exo-/-}$ mouse which exhibits at least one symptom of aging, wherein the symptoms of aging are selected from the group consisting of abnormalities in tissues of high cellular turnover, heart dysfunction, graying hair and alopecia, auditory function loss, cochlear degeneration, immune cell loss, anemia, male germ cell loss leading to lack of sperm and infertility, skeletal muscle mass loss (sarcopenia), loss of bone mass, neurodegeneration, increased presence of apoptic stress markers, and decreased mitochondrial function.

DETAILED DESCRIPTION OF THE INVENTION

In General

Figure 1:
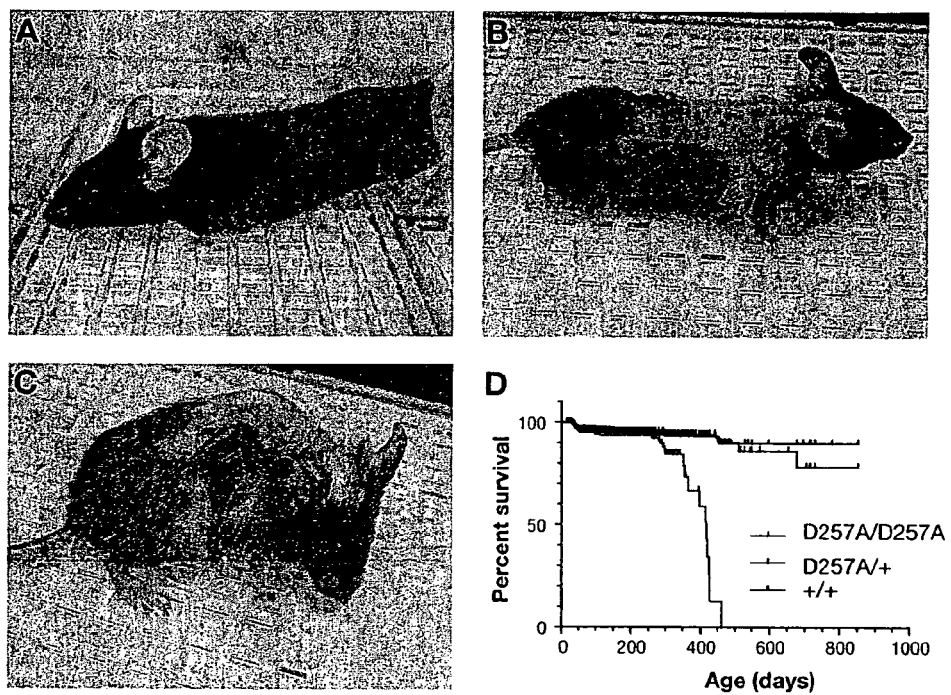
FIG. 1. D257A mice display a premature aging phenotype. Shown are wild-type (A) and D257A mice (B and C) at ~13 months of age. Progeroid symptoms including hair loss, graying, and kyphosis become apparent at ~9 months of age and progress rapidly thereafter. (D) Kaplan-Meier survival curve of cohorts of wild-type (+/+), D257A heterozygous mice (D257A/+) and D257A homozygous mice (D257A/D257A). Mice were of a mixed 129/ICR/B6 genetic background. At least 230 mice per genotype are represented in the survival curves.

Mutations in mitochondrial DNA (mtDNA) accumulate in a variety of tissues of mammalian species and contribute to aging through poorly defined mechanisms. We have addressed this issue by characterizing mice that express a proof-reading deficient version of the mitochondrial DNA polymerase gamma (Polg) and accumulate mtDNA mutations in at least two tissues, preferably in both mitotic and post-mitotic tissues described below. Accelerated aging in these animals is characterized by marked alterations in organs displaying rapid cellular turnover, such as the intestinal epithelium, testis and thymus, as well as loss of skeletal muscle mass, heart dysfunction, hearing loss, graying and alopecia. Accumulation of mtDNA mutations is not associated with increased markers of oxidative stress, but is correlated with the induction of apoptosis in target tissues.

We have engineered an animal model of accelerated aging. The present invention broadly relates to a transgenic mouse model for mammalian aging including a mouse having a genomic mutation in an exonuclease domain of a mitochondrial DNA polymerase gamma (Polg) gene. We envision that mutations in the ExoI, ExoII or ExoIII domains would be suitable, as described below.

Mouse Model

Specifically, one embodiment the present invention provides for a transgenic mouse model for mammalian aging. Preferably, the mouse has a genomic mutation in an exonuclease domain, preferably ExoII, of a mitochondrial DNA polymerase gamma (Polg) gene. The impairment of the exonuclease domain activity results from the expression of a DNA proof-reading deficient version of the mitochondrial DNA polymerase gamma (Polg) gene and accumulation of mitochondrial DNA mutations in both mitotic and post-mitotic mouse tissues, which is correlated with the activation of caspase-3 and the induction of apoptosis in mouse tissues.

The examples below show creation of a POLG mutation in mice derived from 129 SV AB2.2ES cells. However, we believe that the mutation can be introduced into any mouse strain with successful results because the same type of mutation would work similarly in any mouse strain. As with the mouse model described below in the Examples, one would typically target one of the exonuclease domains of mitochondrial DNA polymerase gamma (Polg) gene, preferably that gene described at NM_017462. N. Lecrenier, et al., Gene 185:147–152, 1997, incorporated by reference, discloses the sequence and characterization of mitochondrial DNA polymerase.

By "exonuclease domain" we mean nucleotides at 819–836, 1026–1067 or 1413–1442, as numbered in NM_017462 or SEQ ID NO:1. SEQ ID NO:2 is the amino acid sequence of the wild-type POL gene. SEQ ID NO:3 is the sequence of a preferred POLG mutations, D257A.

The examples below show the creation of the genetically manipulated "knock-in" mouse from embryonic stem cells. This is a preferred method of creating a transgenic mouse of the present invention.

In one preferred embodiment, the mutation is a double base substitution (AC to CT) at residues 1054 to 1055 of ExoII in the mouse Polg gene, as numbered in NM_017462. However, we believe that other mutations will be equally suitable for the present invention. As described above, the mouse must accumulate mtDNA mutations in at least two tissues. One may review the examples to determine how this accumulation is best measured. The present invention specifically includes other mutations that will result in a mt mutation accumulation. For example, one may wish to do single or double base mutations between residues 819–836 (ExoI), 1026–1067 (ExoII) or 1413–1442 (ExoIII) of the POLG gene.

The mouse model exhibits symptoms of aging which include, but are not limited to, abnormalities in tissues of high cellular turnover, heart dysfunction, graying hair and alopecia, auditory function loss, cochlear degeneration, immune cell loss, anemia, male germ cell loss leading to lack of sperm and infertility, skeletal muscle mass loss (sarcopenia), neurodegeneration, increased presence of oxidative stress markers, and decreased mitochondrial function. The primary symptoms would be the following: impaired hearing function and heart function, loss of bone and muscle mass and, at the molecular basis, the induction of apoptosis.

Method of Screening

Another embodiment of the invention provides a method of screening for a potentially therapeutic agent useful for delaying the onset of aging-related symptoms. The method includes providing a mouse model as described above, wherein the mouse exhibits aging-related symptoms and administering the agent to the mouse model. One would then determine whether the agent is capable of delaying the onset of aging-related symptoms in the mouse model treated with the agent compared to an untreated mouse model. Specifically, one may wish to examine either singly or a set of symptoms selected from the group consisting of abnormalities in tissues of high cellular turnover, heart dysfunction, graying hair and alopecia, auditory function loss, cochlear degeneration, immune cell loss, anemia, male germ cell loss leading to lack of sperm and infertility, skeletal muscle mass loss (sarcopenia), neurodegeneration, loss of bone mass and increased presence of oxidative stress markers. Preferably, one should administer the compound to the mice early in life, and measure survival rates and organ function later in life.

In a related embodiment, the invention provides a method of screening for a potentially therapeutic agent useful for treating medical conditions such as progressive external ophthalmoplegia, sensorimotor polyneuropathy, ataxia, Parkinson's syndrome or early menopause. The agent could be an agent that acted at the genetic level, at a pharmaceutical level or is a dietary product.

Generation of a Mouse Model

In yet another embodiment, the invention provides a method of generating a mouse model for mammalian aging. The method includes introducing into a mouse a germline transmission of a mutation in an exonuclease domain, preferably exonuclease domain II, of a mitochondrial DNA polymerase gamma (Polg) gene as described above. Preferably, the mutation is a double base substitution (AC to CT) at residues 1054 to 1055 of the mouse Polg gene. The mutation results in the production of a $polg^{exo-/+}$ mouse. One would then typically crossbreed the $polg^{exo-/exo+}$ mouse and generate a homozygous $polg^{exo-/exo-}$ mouse which exhibits at least one symptom of aging, wherein the symptoms of aging are selected from the group consisting of abnormalities in tissues of high cellular turnover, heart dysfunction, graying hair and alopecia, auditory function loss, cochlear degeneration, immune cell loss, anemia, male germ cell loss leading to lack of sperm and infertility, skeletal muscle mass loss (sarcopenia), neurodegeneration, increased presence of oxidative stress markers, and decreased mitochondrial function.

EXAMPLES

Figure 9:
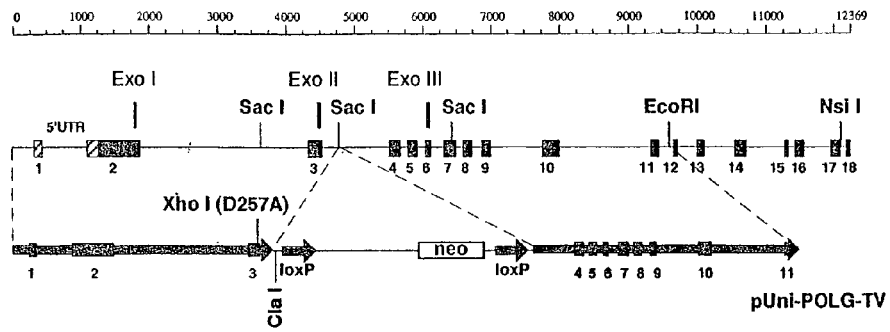
FIG. 9. Generation of D257A mice. (A) A ~12.3 Kb genomic region containing all three exonuclease domain encoding sequences of POLG, ExoI, ExoII and ExoIII is shown. We constructed a targeting vector containing two arms of homologous DNA, approximately 5 Kb in length each. The neo selectable marker was flanked with loxp sites (which are not drawn to scale). On the 5' targeting vector arm we introduced an AC to CT double base substitution at positions 1054–55 of the mouse PolgA mRNA using a PCR based site-directed mutagenesis strategy, resulting in the introduction of a novel XhoI site. (B) Structure of targeted PolgA locus following successful homologous recombination. (C) Mice carrying the the D257A mutation were crossed to Cre recombinase expressing transgenic mice, resulting in the removal of the region flanked by loxP sites, including the neo selectable marker. Only a small region containing a single loxP site remains after recombination. (D) Southern analysis of gene targeting in ES cells. Following electroporation, ES cells clones were selected in G418 containing media and expanded. DNA extracted from individual clones was digested with NsiI and ClaI, and probed with a 5' external probe. The asterisk denotes an ES clone that carries both the targeted $PolgA^{257Aneo}$ and wild-type alleles.
Figure 9:
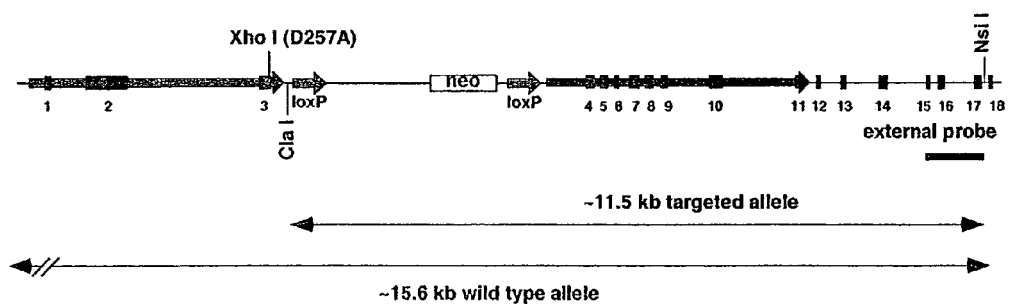
Figure 9:
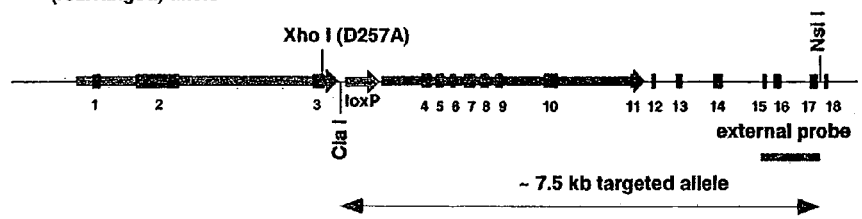
Figure 9:
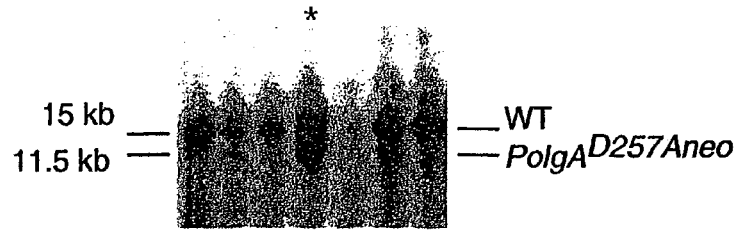
Figure 10:
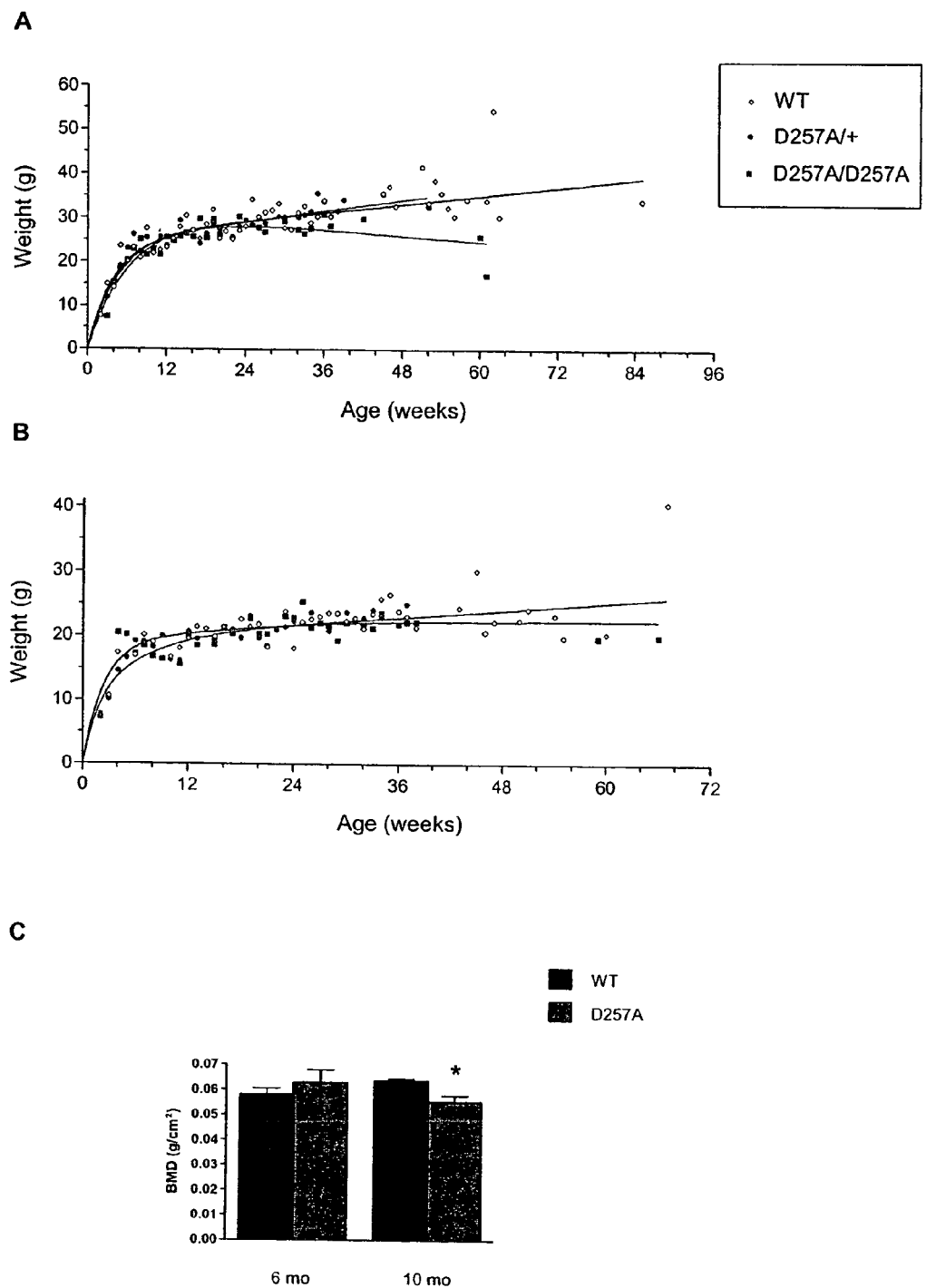
FIG. 10. Body weight and bone mineral density as a function of age. (A) Body weight of males, (B) Body weight of females, (C) Bone mineral density (femur) in males and females combined. Wild-type and D257A mice at approximately 6 months and 10 months of age were anesthetized with 240 mg/kg tribromoethanol, secured to an lightly adhesive tray and subjected to X-ray densitometery using a PIXImus™ densitometer (GE Lunar, Madison Wis.). Bone mineral density (BMD) was calculated using PIXImus software version 1.45.

Mitochondrial DNA Mutations, Oxidative Stress and Apoptosis in Mammalian Aging mtDNA mutations lead to a premature aging phenotype. Mitochondrial DNA replication in mammalian cells lacks DNA mismatch repair, relying solely on the 3'–5' exonuclease activity of POLG to correct DNA mismatches that arise due to nucleotide misincorporation during DNA replication. We cloned the locus encoding the catalytic subunit of mouse POLG, PolgA, and used gene targeting in embryonic stem cells to introduce a AC to CT two base substitution at position 1054–1055 of the PolgA cDNA (FIG. 9). This mutation results in a critical aspartate to alanine residue substitution in the second conserved exonuclease domain of POLG. This substitution profoundly impairs the proofreading ability of mouse POLG (A. Trifunovic, et al., supra, 2004), and the equivalent mutation in yeast POLG results in a marked increase in the mtDNA mutation rate (F. Foury and S. Vanderstraeten, *EMBO Journal* 11:2717–26, 1992). Germline transmission of the mutation resulted in the production of $polgA^{D257A/+}$ mice, which were intercrossed to generate homozygous $PolgA^{D257A/D257A}$ mice, hereafter denoted D257A. Although we expected that D257A mice would display a mtDNA mutator phenotype, we observed no evidence of embryonic lethality or developmental abnormalities in these animals. Young D257A mice were indistinguishable from wild-type littermates, but long-term follow up revealed a striking premature aging appearance beginning at ~9 months of age, consisting of hair loss, graying and kyphosis (FIG. 1A to C). These observations were associated with a reduced lifespan (maximum survival of 460 days as compared with >852 days for wild-type littermates, P<0.0001, FIG. 1D). We also observed an age-related decrease in body weight and bone density (FIG. S2), which is a hallmark of aging in rodents (H. R. Massie, et al., *Exp. Gerontol.* 25:469–481, 1990) and humans (E. Seeman, *J. Appl. Physiol.* 95:2142–2151, 2003). Although initially fecund, we observed sterility of both male and female D257A animals at ~5 months of age.

Figure 2:
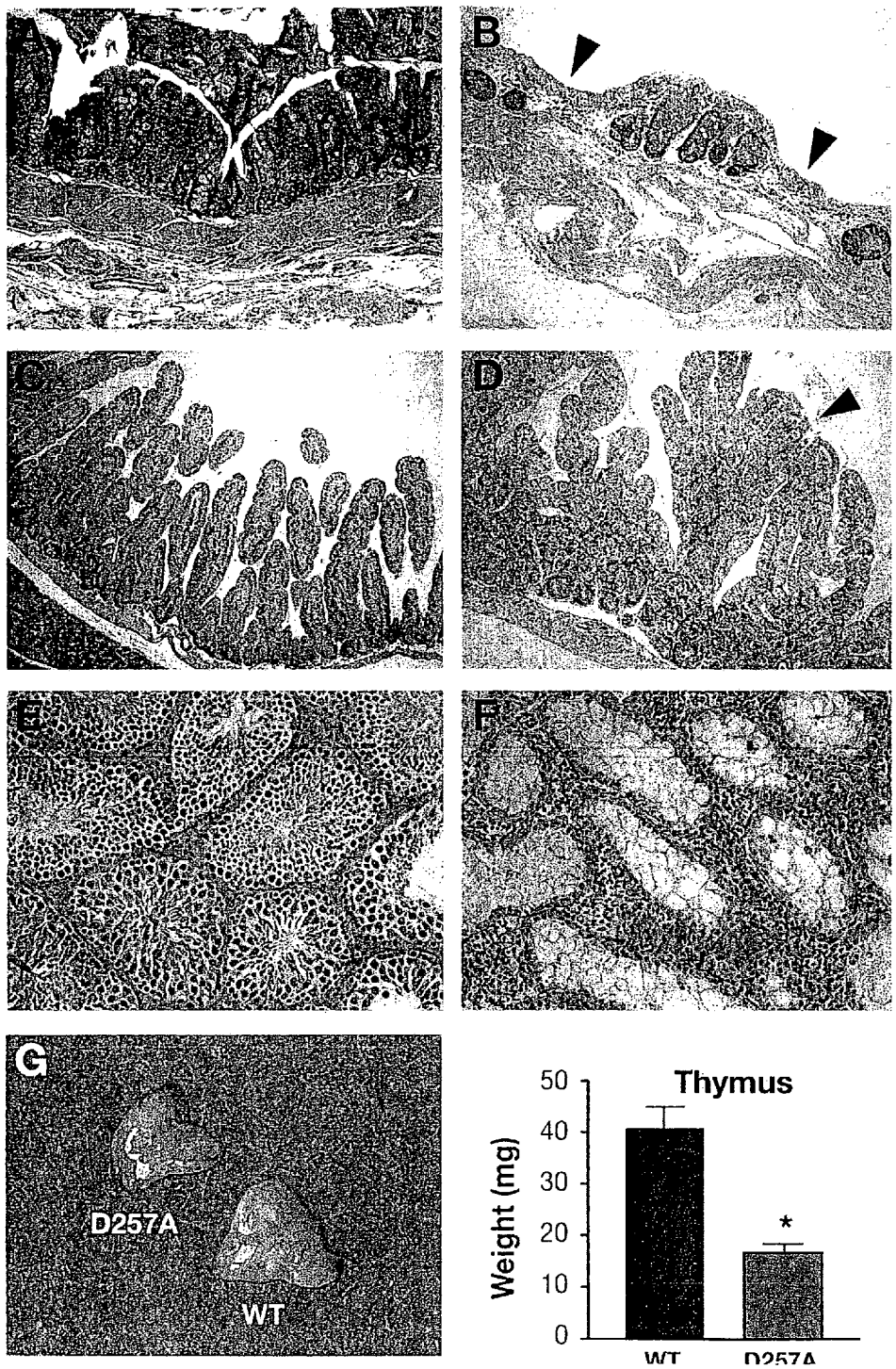
FIG. 2. D257A mice develop abnormalities in tissues of high cellular turnover. Shown are H&E-stained sections from wild-type (A and C) and D257A (B and D) duodenum and cecum at ~10 months of age. Large regions of the cecum display reduced number of crypts (B) and aberrant vilar fusion and branching is observed in the duodenum (D). Testicular cross sections of wild-type (E) and D257A (F) showing loss of spermatogonia and sperm in D257A animals at 10 months of age. Abnormal testicular architecture is observed initially at ~5 months of age. The thymus is reduced in size (G) and weight (H) in D257A mice at 3 months of age (*P<0.0003).
Figure 11A:
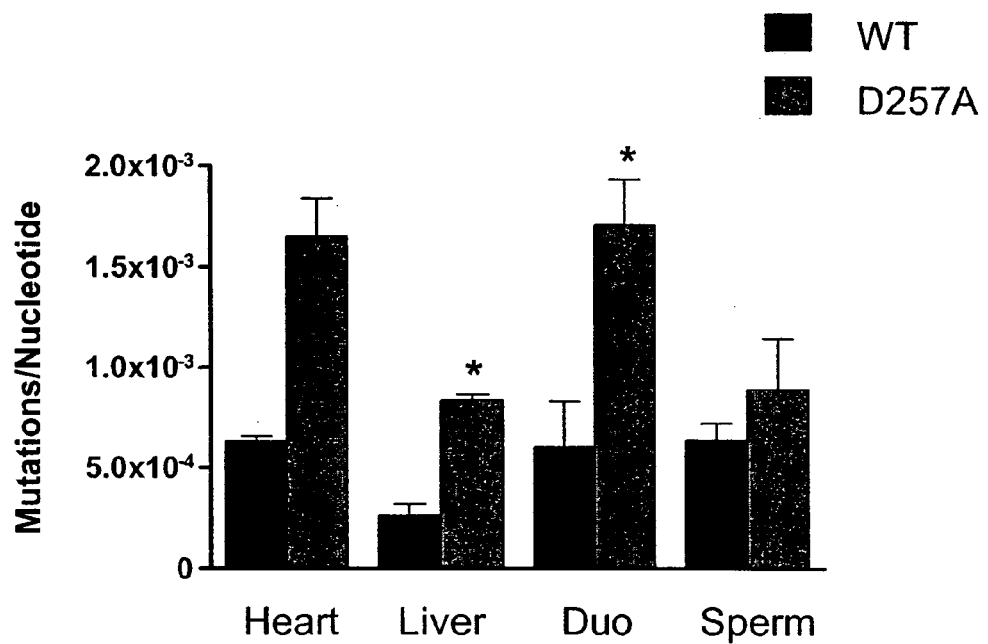
FIG. 11. Sequencing of mtDNA in various tissues of wild-type and D257A mice. We isolated mitochondria from heart, duodenum (duo) and liver from from individual wild-type and D257A animals at 5–6 months of age. Mitochondrial DNA was isolated and digested with DraIII and BgIII followed by treatment with exonuclease III in order to degrade any contamination with nuclear DNA. A 525 bp mtDNA fragment that spans a portion of the D-loop region and mt-Cytb (cytochrome b) gene was PCR amplified and cloned into the pCR4-TOPO cloning vector. One hundred ninety-two clones from each tissue source, representing ~100,000 bp, were sequenced and the DNA sequences aligned using Aligner software (Codon Code). The frequency of PCR— and cloning-induced mutations ($1/16,000$ bp), was determined by reamplifying, cloning and sequencing individual clones. (A) Tissue distribution of mtDNA mutations in wild-type and D257A mice after background substraction. Two animals were used for each tissue/genotype. (B) Mutational spectrum in wild-type and D257A mice. Transition mutations represented the largest class of mutations in all tissues examined. Transversions varied greatly in tissues of wild-type mice (3–26%), and represented a higher proportion of mutations in the heart (26%) of wild-type tissues. The proportion of transversions was higher (16–25%) and more uniform in the D257A tissues, consistent with the fact that most mtDNA mutations in D257A mice are likely to arise from the same mechanism, nucleotide misincorporation by POLG. The total number of mutations represented in the graph ranged from 110 (sperm, wild-type) to 637 (heart, D257A).
Figure 11B:
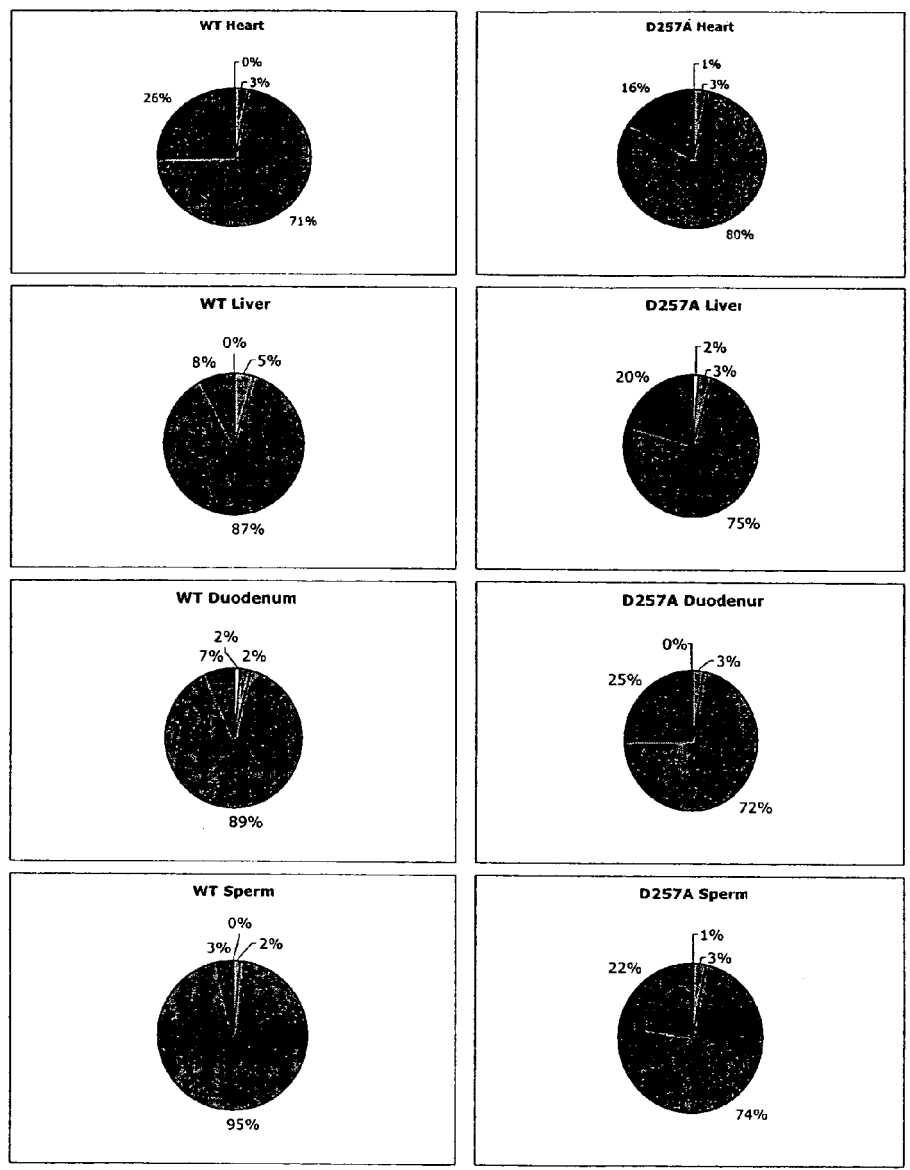

To examine if mtDNA mutations accumulate to an equal extent in mitotic and post-mitotic tissues of D257A mice, we performed large-scale sequencing of a 525 bp region of mtDNA that spans the control region and a fragment of the gene encoding cytochrome b. Tissues were derived from heart, liver, duodenum and sperm of ~6-month-old D257A mice and wild-type controls. DNA sequencing of over 300,000 bp of mtDNA for each tissue revealed that D257A mice display a frequency of mtDNA mutations in this region that is ~3 times the level observed in wild-type animals for all tissues examined except sperm, which displayed only a slight increase (~35%) in mutation frequency (FIG. 11). Possibly, selection for viable sperm results in the elimination of sperm that carry high mtDNA mutational loads. Most mutations were transition mutations, with the level of transversions varying greatly in wild-type tissues (3–26%), and less so in D257A tissues (16–25%) (FIG. 11). These observations suggest that different mechanisms contribute to the mutational spectrum of mtDNA in various tissues of wild-type mice, but reduction of mtDNA replication fidelity is the major mutational mechanism in mtDNA of D257A mice. Surprisingly, we find that the frequency of mtDNA mutations in 6-month-old wild-type mice is as high as $6.7 \times 10^{-4}$ mutations/bp, representing over 10 mutations/mitochondrial genome. Our findings indicates that large levels of mtDNA mutations exist in adult animals in both mitotic and post-mitotic tissues, and that further age-related accumulation of mtDNA mutations may contribute to several aging phenotypes. The modest increase (~3-fold) in mtDNA mutation frequency reported here for D257A mice is surprising in view of the dramatic phenotype observed in these animals, the severe impact of this mutation on exonuclease activity in vitro (A. Trifunovic, et al., supra, 2004), and the marked increase in mitochondrial mutation frequency in yeast carrying the equivalent mutation (F. Foury, S. Vanderstraeten, supra, 1992). This observation suggests that mitochondria that harbor large numbers of mutated mtDNA molecules are degraded, or that cells that carry large numbers of such mutations do not survive.

mtDNA mutations impact tissues of high cellular turnover. We next performed necropsy and histological examination of D257A mice of various ages. A remarkable phenotype was dysplasia of the intestinal epithelium, characterized by an age-related loss of crypts in some regions of the cecum (FIGS. 2A and B), villar fusion, and complex villar branching in regions of the duodenum (FIGS. 2C and D). The intestinal epithelium is a tissue of very high cellular turnover, and it appears to be particularly susceptible to the accumulation of mtDNA mutations and subsequent loss of tissue homeostasis. This finding is of interest given the recent report of accumulation of pathogenic mtDNA mutations in human colonic crypt stem cells with aging (R. W. Taylor, et al., *J. Clin. Invest.* 112:1351–1360, 2003). We also observed reduced testicular size and a progressive depletion of spermatogonia in the testis of D257A mice, leading to a degeneration of the seminiferous epithelium by ~6 months of age (FIGS. 2E and F). Sperm are generated continuously throughout reproductive life through germline cell division, and therefore germline stem cells are likely to accumulate high levels of mtDNA mutations in D257A mice.

Figure 12:
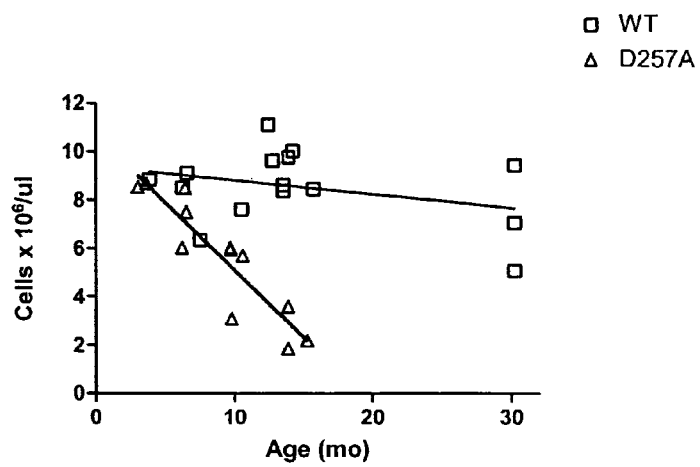
FIG. 12. Red blood cell counts. (A) Red blood cell counts in individual wild-type and D257A mice plotted versus age. (B) Mean red blood cell counts in young and old wild-type mice. Means were compared by t test; *P<0.05.
Figure 12:
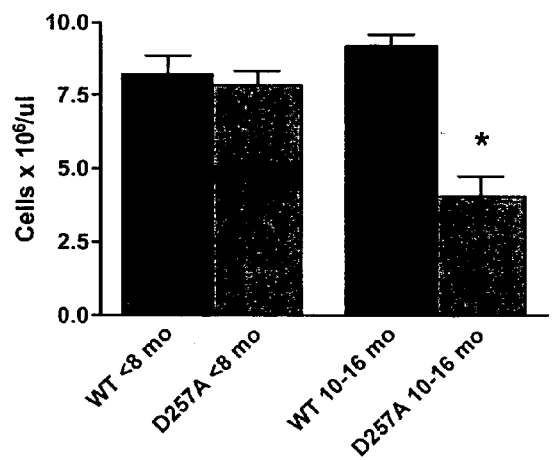

Thymic atrophy is a common aging phenotype in several mammalian species. We observed that the earliest detectable phenotype of D257A mice is a profound thymic atrophy starting at 2–3 months of age (FIG. 2G). Thymus weight is 40.6±4.4 mg in wild-type mice as compared to 16.0±1.88 mg in D257A mice at 3 months of age (P<0.0003, FIG. 2H). Hematopoietic stem cell precursors of mature T-cells originate from the bone marrow and migrate to the thymus, which is the major site of T-lymphocyte maturation. Within the cortex of the thymus, precursors of T cells undergo extensive cell proliferation, but more than 95% of thymocytes die by apoptosis before they reach the medulla and the blood stream (K. Abbas, A. H. Litchman, J. S. Pober, in *Cellular and Molecular Immunology*, A. K. Abbas, A. H. Litchaman, J. S. Pober, Eds. (Saunders, Philadelphia, 1997), pp. 171–193). Thus, thymic atrophy in D257A may be due to reduced cellular proliferation, increased apoptosis, or both. We did not observe overt depletion of hematopoietic cells in the bone marrow of D257A mice. However, loss of bone marrow homeostasis seems likely given that red blood cell counts were reduced significantly in D257A mice as a function of age (FIG. 12). Hair graying in aging in humans and mice has recently been linked to loss of melanocyte stem cells (E. K. Nishimura, et al., *Science* 2004 Dec 23; Epub ahead of print), and D257A mice display early onset graying (FIGS. 1B and C). When taken as a whole, this collection of phenotypes suggests that accelerated aging associated with mtDNA mutations in D257A mice is at least partly due to depletion of stem cell progenitors and loss of homeostasis in highly proliferative tissues.

Figure 3:
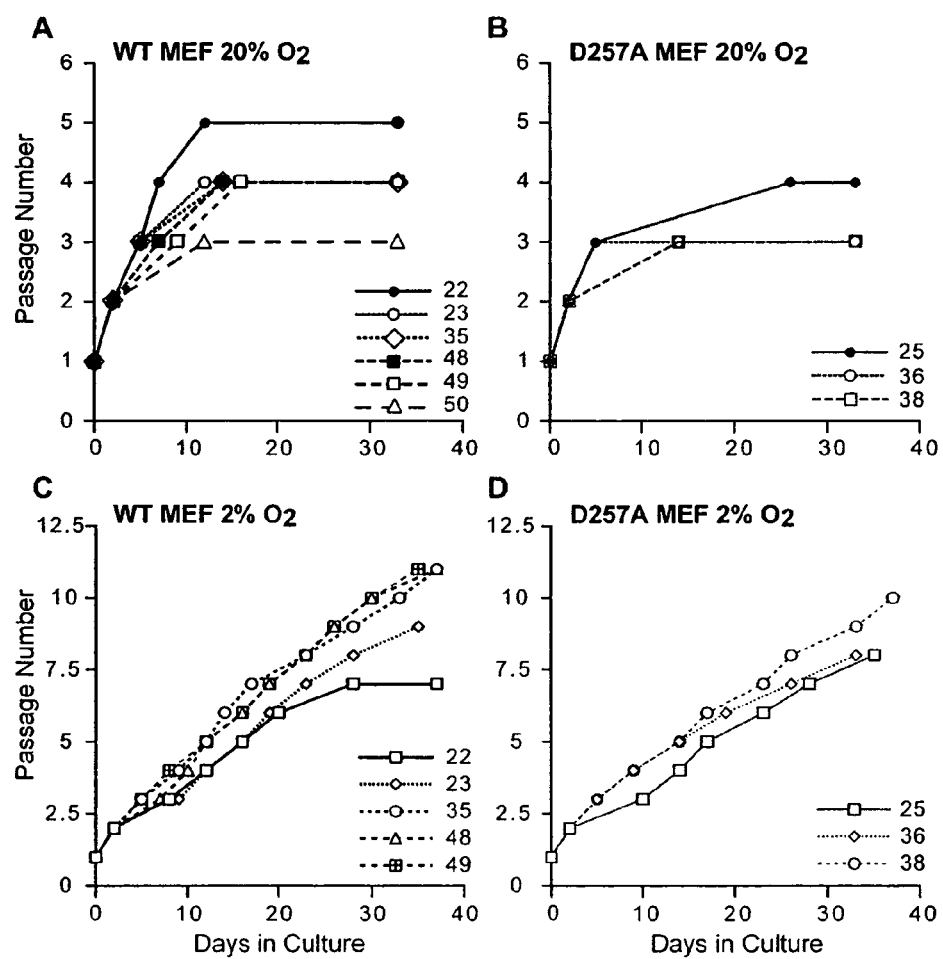
FIG. 3. mtDNA mutations and replicative senescence. Mouse embryonic fibroblasts (MEF) were derived from individual embryos. Cultures were passaged using a 1:4 subculture regimen and incubated at 37° C. in a normoxic atmosphere of 75% $N_2$, 5% $CO_2$, and 20% $O_2$ (A and B) or a hypoxic atmosphere of 93% $N_2$, 5% $CO_2$, and 2% $O_2$ (C and D). Wild-type cell lines: 22, 23, 35, 48, 49 and 50. D257A cell lines: 25, 36 and 38.
Figure 4:
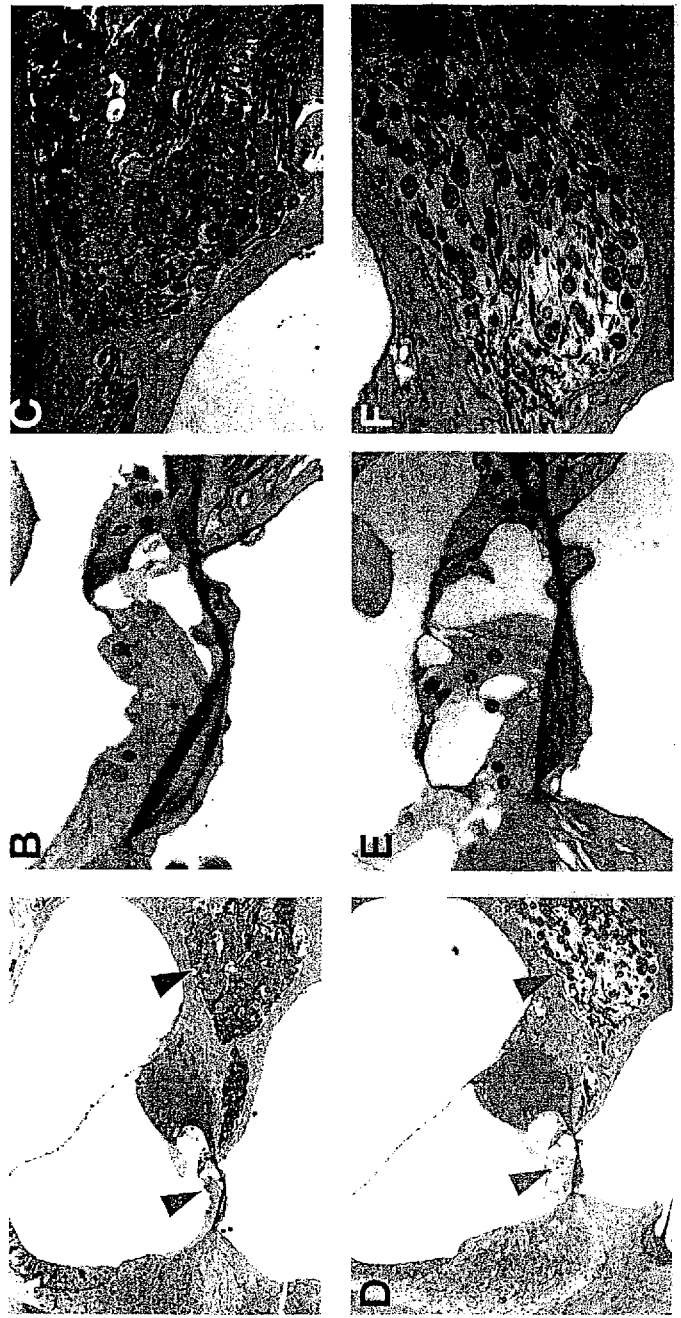
FIG. 4. Age-related loss of auditory function and cochlear degeneration in D257A mice. Cochlea from wild-type (A, B and C) and D257A (D, E and F) animals. Arrows in panel A indicate hair cell and spiral ganglion neuronal cell regions shown in panels B and C respectively. D257A mice display preservation of cochlear hair cells (E) and severe loss of spiral ganglion neuronal cells (F) by 9 months of age. (G and H) Means of auditory-evoked brain stem response (ABR) thresholds (dB SPL) for wild-type and D257A mice at 4, 8 and 16 kHz. Means are not different between 2-month-old wild-type and D257A mice (G), but are markedly elevated in 9-month-old D257A mice (N=5, P<0.0001) (H), indicating loss of auditory function.
Figure 4:
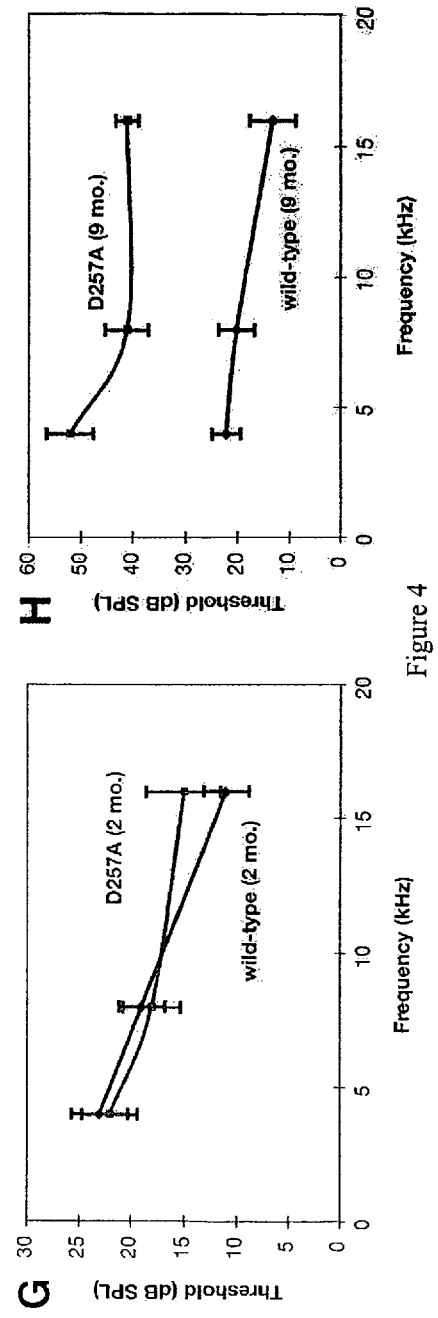

One possible mechanism for the D257A phenotypes described above is a defect in cellular proliferation associated with the accumulation of mtDNA mutations. In order to characterize the effects of the D257A mutation and subsequent accumulation of mtDNA mutations on replicative senescence, we derived several independent mouse embryonic fibroblasts lines (MEFs) from D257A and wild-type littermates and measured the number of cell doublings prior to senescence. Passaging of wild-type MEFs under normal, high-oxygen tension (20%) leads to rapid senescence associated with oxygen toxicity, whereas passaging MEFs under low oxygen tension (2%) does not lead to replicative senescence (S. Parrinello, et al., *Nat. Cell Biol.* 5:741–747, 2003). At 20% oxygen, both wild-type and D257A MEFs underwent rapid senescence (FIGS. 3A and B). In contrast, we did not observe senescence or reduced growth of either wild-type or D257A MEFs following over 40 days of tissue culture (FIGS. 3C and D). Thus, accelerated aging in D257A mice is not likely to be due to an intrinsic defect in cellular proliferation.

mtDNA mutations result in accelerated age-related hearing loss, sarcopenia and heart dysfunction. We next examined post-mitotic tissues known to play critical roles in mammalian aging. Age-related hearing loss (presbycusis) is a hallmark of aging in multiple species, including mice (Q. Y. Zheng, et al., *Hear. Res.* 130:94–107, 1999), and in humans it affects over 60% of individuals aged 70 or older (M. A. Gratton and A. E. Vazquez, *Curr. Clin. Otolaryngol. Head Neck Sur.* 11:367–371, 2003). Presbycusis is associated with the age-related accumulation of mtDNA mutations in auditory tissue, although a causal nature for this relationship has not been established (M. D. Seidman, et al., *Arch. Otolaryngol. Head Neck Surg.* 123:1039–1045, 1997; M. D. Seidman, *Laryngoscope* 110:727–738, 2000). Hearing loss can be monitored by an elevation in auditory-evoked brainstem responses (ABR). We conducted an ABR threshold analysis in young (2 months) and old (9 months) D257A mice and wild-type littermates. Our results revealed no difference in auditory function between wild-type and D257A mice at 2 months of age (FIG. 4G), but we found marked elevation of ABR thresholds at 4, 8 and 16 kHz (P<0.0001) in D257A mice by 9 months of age, indicating severe hearing loss (FIG. 4H). Histological analysis revealed age-related loss of spiral ganglion neurons (FIGS. 4C and F), a common feature of age-related hearing loss (S. L. McFadden, et al., *Audiology* 40:313–321, 2001; E. M. Keithley, et al., *Hear. Res.* 188:21–28, 2004). Thus, the age-related accumulation of mtDNA mutations can have a causal role in presbycusis.

Figure 13A:
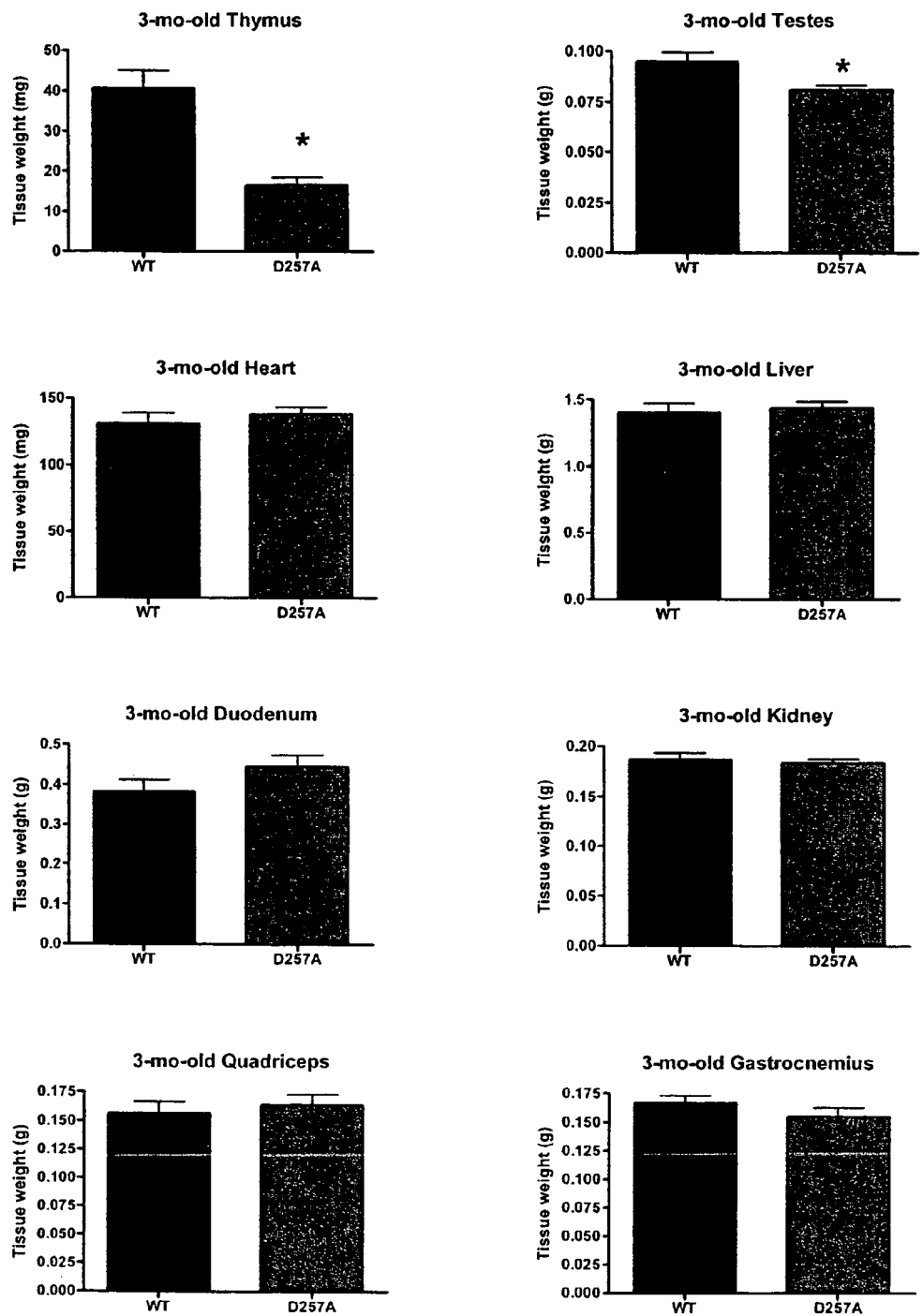
FIG. 13. Organ Weights. (A) Organ weights in wild-type and D257A mice at 3 months of age. (B) Organ weights in wild-type and D257A mice at 3 months of age. Means were compared by t test; *P<0.05.
Figure 13B:
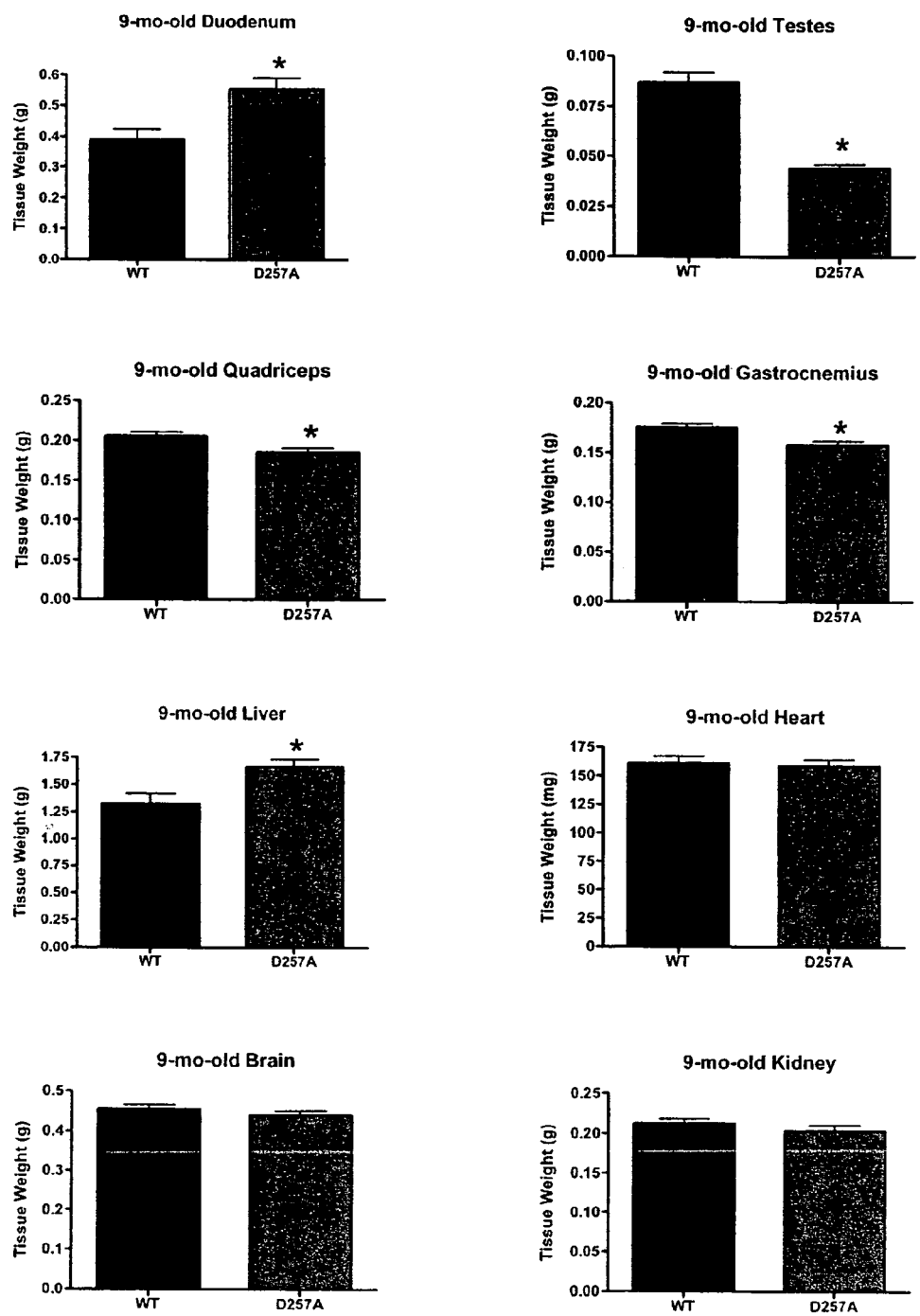

Aging in rodents (J. Wanagat, et al., *FASEB J.* 15:322–332, 2001), rhesus monkeys (N. G. Gokey, et al., *Aging Cell* 3:319–326, 2004) and humans (J. Lexell, et al., *J. Neurol. Sci.* 84:275–294, 1988) is also characterized by loss of muscle mass (sarcopenia) and associated frailty. This loss of muscle mass has been correlated with the accumulation of mtDNA mutations (J. W. Pak, et al., *Aging Cell* 2:1–7, 2003), but there is no direct evidence linking age-related, sporadic mtDNA mutations and sarcopenia. Consistent with a causal role for mtDNA mutations in sarcopenia, we observed muscle loss in 9-month-old D257A mice (FIG. 13). Specifically, muscle weights were significantly reduced in both gastrocnemius (p<0.002, ~10% decrease) and quadriceps (p<0.005, ~10% decrease) muscles of D257A mice at 9 months of age (FIG. S5). We note that this difference was not observed between D257A and wild-type mice at 3 months of age (FIG. 13), and also that at 9 months of age D257A mice are not cachexic, indicating that the decline in muscle mass is age-related and not likely to be an indirect consequence of physiological decline in D257A mice. Therefore, age-related accumulation of mtDNA mutations is likely to be a contributing factor in age-related sarcopenia and associated frailty.

Figure 5:
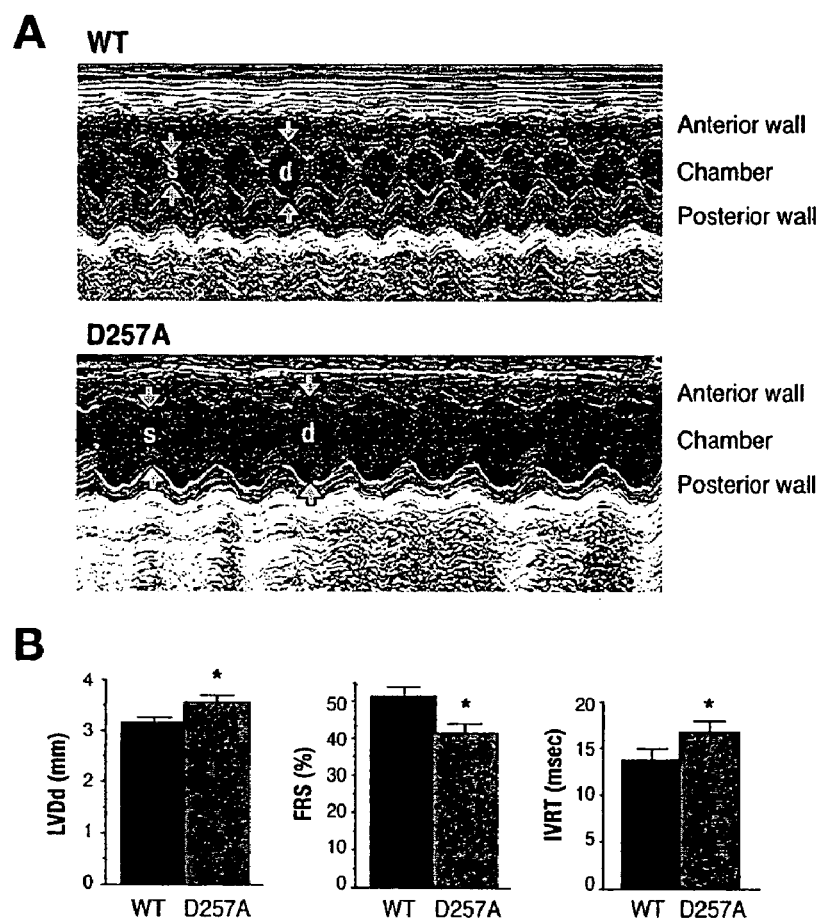
FIG. 5. Age-related heart dysfunction in D257A mice. Echocardiograms of 9–10 month-old wild-type (A) and D257A mice (B). Anterior and posterior walls are relative to instrument location (chest). Wave forms represent individual heart beats, with maximal and minimal chamber size at systole (s) and diastole (d) respectively indicated by arrows. Aging in D257A mice is associated with heart chamber enlargement and loss of contractile function, as determined by impaired diastole (d). (C) LVDd, left ventricular diameter at diastole. FRS, % fractional shortening. IVRT, isovolumic relaxation time. Nine wild-type and D257A mice were used for measurements. *P<0.05.
Figure 6:
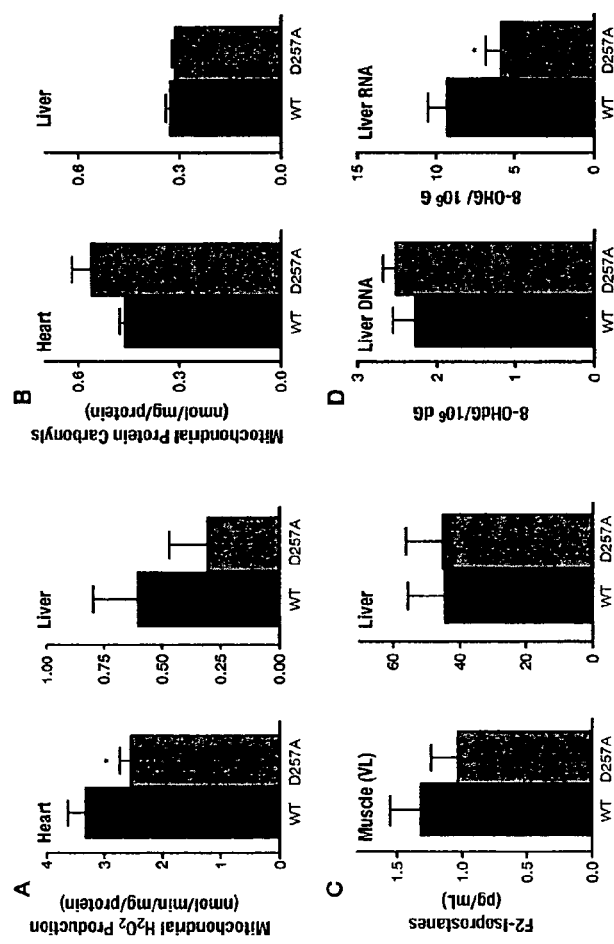
FIG. 6. Oxidative stress markers in isolated mitochondria and tissues from D257A mice. (A) hydrogen peroxide production in isolated mitochondria from wild-type and D257A mice at ~9 months of age. (B) Protein carbonyl levels, a marker of protein oxidation, was measured by western blotting in isolated mitochondria from wild-type and D257A mice at 9 months of age. (C) F2-isoprostanes, a marker of lipid peroxidation, was measured by gas chromatography/ negative ion chemical ionization mass spectrometry in liver and skeletal muscle (vastus lateralis) tissues from 6-month-old wild-type and D257A mice. (D) Oxidative damage to DNA (8-oxo-dG) and RNA (8-oxo-G), was measured by HPLC in liver tissue of 9-month-old wild-type and D257A mice. Nine wild-type and D257A mice were used for hydrogen peroxide production, mitochondrial carbonyl analysis, and nucleic acid oxidative damage assays. Six wild-type and D57A mice were used for F2-isoprostanes measurements. *P<0.05.

The heart is one of the most energy demanding organs in mammals, with up to 35% of cardiomyocyte volume taken up by the mitochondria (R. P. Crisman, et al., *Am. J. Physiol.* 248:H8–H14, 1985). Because of this dependence of the heart on high mitochondrial density, one might expect impaired structure and/or function in the heart of D257A animals. In fact, mtDNA mutations accumulate with aging in the heart, but to what extent this contributes to either age-associated cardiac pathology or the decline in heart function that occurs with normal aging is not clear. Previously reported histological data in D257A mice (Trifunovic, et al., supra, 2004) and mice carrying a heart-specific mutator POLG (D. Zhang, et al., *Genomics* 69:151–161, 2000) suggests that mtDNA mutations lead to age-related heart hypertrophy. To assess left ventricular (LV) systolic and diastolic function as well as structure, we used in vivo M-mode and Doppler echocardiography in D257A and wild-type controls at 12 months of age. We observed increased heart chamber size and LV dilation in D257A mice (FIGS. 5A and B). Additionally, we noted that this dilation was associated with normal wall thickness but a significant decrease in percent fractional shortening (FRS), a measure of heart contraction (FIG. 5B). Thus, D257A mice have a dilated, hypocontractile LV hypertrophy. Interestingly, isovolumic relaxation time (IVRT), a measure of diastolic function, was significantly prolonged in D257A animals (FIG. 5B), consistent with the impaired LV relaxation that occurs with normal aging in rodents and humans (D. A. Brenner, et al., *Circulation* 104:221–226, 2001; P. Spirito and B. J. Maron, *Br. Heart J.* 59:672–679, 1988; P. S. Hees, et al., *Am. J. Physiol. Heart Circ. Physiol.* 286:H782–J788, 2004).

mtDNA mutations and oxidative stress. It is estimated that 2 to 3% of the oxygen consumed by aerobic cells results in the production of superoxide ($O_2$—), which is converted to hydrogen peroxide ($H_2O_2$) by superoxide dismutase. The basic tenet of the free radical theory of aging (D. Harman, *J. Gerontol.* 11:298–300, 1956) is that aging-related loss of function is due to the progressive accrual of damage inflicted by ROS. Importantly, mitochondria are thought to produce most cellular ROS, and ROS can induce damage to DNA, lipids and proteins. The original hypothesis has been refined with a ROS mtDNA mutation hypothesis, according to which aging may be caused by accumulation of ROS-mediated mtDNA mutations over time (J. E. Fleming, et al., supra, 1982). It is further postulated that accumulation of mtDNA mutations leads to a "vicious cycle", further increasing ROS generation and mitochondrial dysfunction (J. E. Fleming, et al., supra, 1982; M. K. Shigenaga, et al., *Proc. Natl. Acad. Sci. USA* 91:10771–10778, 1994). We tested this hypothesis by isolating mitochondria from the heart and liver of young and old (3 months vs. 9 months) D257A mice and wild-type littermates and measuring hydrogen peroxide production. Surprisingly, we found that $H_2O_2$ production was decreased in heart mitochondria of 9-month-old D257A mice (FIG. 6A). We also assayed mitochondrial protein carbonyls, a marker of oxidative damage to proteins, and found no significant differences in D257A and wild-type animals in mitochondrial (FIG. 6B) or cytosolic fractions of either heart and liver (data not shown). Thus, isolated mitochondria from D257A animals do not show signs of increased oxidative stress.

Because reduced mitochondrial function and associated energetic deficits may reduce cellular antioxidant capacity, we also examined markers of ROS production in tissue extracts of D257A mice. Lipid peroxidation is a central mechanism of ROS-mediated cellular injury, and can be assessed through the measurement of F2-isoprostanes, prostaglandin-like compounds formed in vivo from the free radical-initiated peroxidation of arachidonic acid (L. J. Roberts, $2^{nd}$ and J. D. Morrow, *Cell. Mol. Life Sci.* 59:808–820, 2002). We used a highly sensitive gas chromatography/mass-spectrometry method to measure F2-isoprostanes in liver and skeletal muscle, and observed no differences between D257A mice and wild-type controls (FIG. 6C). We next examined oxidative damage to DNA and RNA in 9-month old wild-type and D257A mice through the measurement of 8-hydroxyguanosine and 8-hydroxydeoxyguanosine using HPLC. We observed no difference in the levels of 8-hydroxydeoxyguanosine levels in liver DNA (FIG. 6D), and observed a significant reduction in the steady state levels of 8-hydroxyguanosine in liver RNA of D257A mice (FIG. 6D, $P<0.05$). Thus, our observations do not support the hypothesis that accumulation of mtDNA mutations contributes to increased ROS production in aging. Instead, our findings demonstrate that aging mediated by mtDNA mutations can occur in the absence of increased oxidative damage to DNA, protein or lipids.

Figure 7:
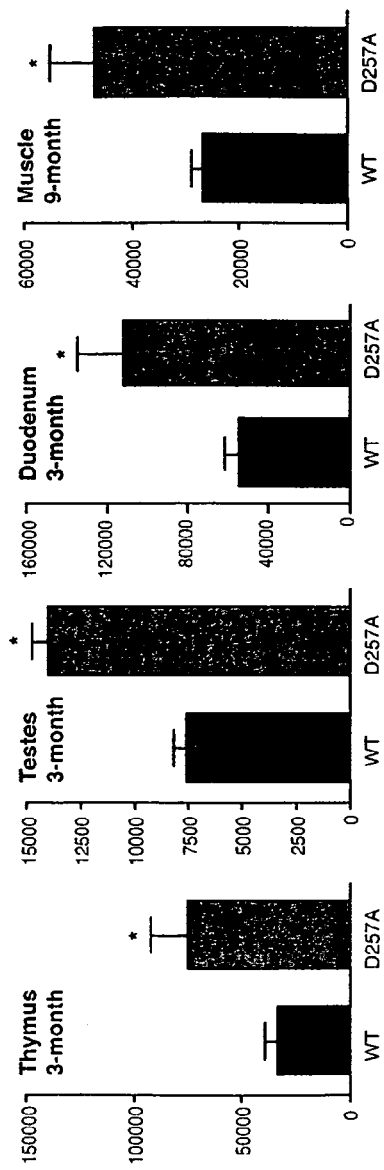
FIG. 7. Caspase activation. Activation of caspase-3 requires proteolytic processing of its inactive zymogen into activated fragments. The specific antibody used detects endogenous levels of the large fragment (17/19 kDa) of activated caspase-3 resulting from cleavage adjacent to Asp175. Extracts of tissues (25 μg) from wild-type and D257A animals of the indicated ages were separated by SDS-polyacrylamide gel electrophoresis (SDS-PAGE) and probed with a mouse monoclonal antibody against cleaved caspase 3. Units are arbitrary OD units. *For all tissues tested, the difference between wild-type and D257A mice was significant (P<0.05).

Apoptosis underlies aging induced by mtDNA mutations. The central signaling component of apoptosis is a proteolytic system involving a family of cysteine proteases called caspases. In the mitochondrial pathway of apoptosis, mitochondrial dysfunction can lead to mitochondrial outer membrane permeabilization (MOMP), the release of cytochrome c into the cytosol, and activation of caspase-3, a key effector caspase found activated in cells committed to death (D. W. Nicholson, et al., *Nature* 376:37–43, 1995). To determine the extent of apoptosis in tissues of D257A mice, we monitored the levels of cleaved caspase-3 in cytosolic fractions. Levels of cleaved caspase-3 were significantly elevated in the cytosolic fractions of testis, duodenum, and thymus of 3-month-old D257A mice (FIG. 7), and this induction preceded overt degeneration in these tissues. In skeletal muscle, levels of cleaved caspase 3 were not significantly altered in 3-month-old D257A mice, but were significantly increased at 9 months of age (FIG. 7), when animals displayed loss of muscle mass. Thus, we hypothesize that activation of caspase-3 and subsequent apoptosis is likely to be a causal event in loss of tissue homeostasis due to age-related accumulation of mtDNA mutations in multiple tissues of D257A mice.

Figure 8:
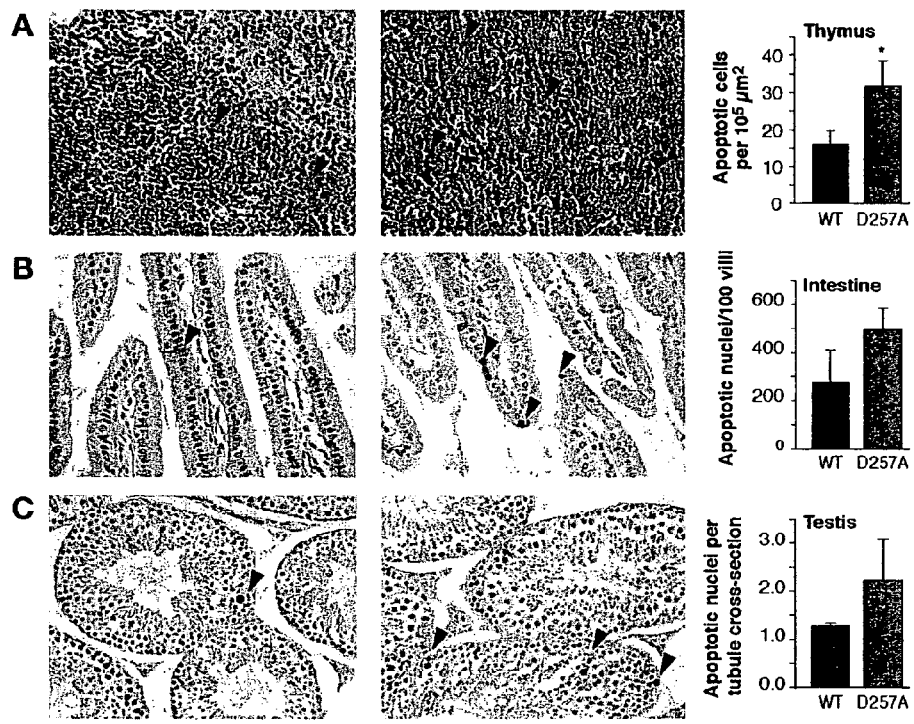
FIG. 8. Apoptosis detection by TUNEL. Arrows indicate TUNEL-positive apoptotic nuclei. Quantification of apoptosis in thymus (A), small intestine (B) and testis (C) of wild-type (left panels) and D257A (center panels). The number of apoptotic nuclei per $10^5$ $\mu m^2$ (thymus), 100 villi (intestine) and tubule cross section (testis) were counted in H&E-stained sections from the indicated genotypes. Each bar represents apoptotic nuclei from intestinal, thymus and testis sections of at least 4 mice/genotype. *P<0.05.

Apoptosis is also associated with nuclear DNA fragmentation and formation of mono- and oligo-nucleosomes. Because the intestinal epithelium, thymus and testis were severely affected in D257A mice, we also examined these tissues with terminal transferase-mediated dUTP nick-end labeling (TUNEL), an assay that detects apoptotic cells in situ. Counting of TUNEL positive cells in the duodenum, testis and thymus of 3-month old D257A mice revealed a consistent trend for elevation of TUNEL positive cells in all tissues examined, and this trend was associated with higher variability in individual D257A mice, as expected from the stochastic nature of mtDNA mutations (FIG. 8). We also determined by ELISA that the content of cytosolic mono- and oligo-nucleosomes (180-base pair nucleotides or multiples) was significantly increased in testis and thymus of 3-month-old D257A mice (data not shown). Taken as a whole, our observations strongly suggest that loss of critical, irreplaceable cells through apoptosis is the central mechanism of tissue dysfunction associated with the accumulation of mtDNA mutations.

Conclusion. The finding that a two-base substitution in the PolgA gene in the context of a $3\times10^9$ bp mammalian genome results in the acceleration of multiple age-related phenotypes is striking. Our observations in D257A mice and those recently described by Trifunovic, et al. in a mouse model that carries the same mutation (A. Trifunovic, et al., supra, 2004) provide strong evidence for a role of mtDNA mutations in organismal aging. Our findings demonstrate that the D257A mutation leads to accumulation of high levels of mtDNA mutations in tissues of high cell turnover, such as the intestine, resulting in loss of tissue homeostasis. We have also functionally characterized post-mitotic tissues in D257A mice, and uncovered defects in heart and auditory function, two systems highly affected by aging in humans. The wide tissue distribution of phenotypes in D257A mice suggests that the accumulation of mtDNA mutations associated with aging is likely to exert serious functional consequences, and that mtDNA mutations contribute to age-related physiological decline. Importantly, we have demonstrated that accelerated aging through a mitochondrial pathway can occur in the absence of increased ROS production, and may be causally linked to increased apoptosis.

The concept that DNA damage contributes to aging is supported by the finding that humans and mice carrying mutations in several genes involved in DNA repair, including XPD (J. de Boer, et al., *Science* 296:1276–1279, 2002), Ku86 (H. Vogel, et al., *Proc. Natl. Acad. Sci. USA* 96:10770–10775, 1999), and WRN(S. Chang, et al., *Nat. Genet.* 36:877–882, 2004), display progeroid syndromes. It is likely that several types of DNA damage contribute to the aging process (P. Hasty and J. Vijg, *Aging Cell* 3:55–65, 2004), and our findings suggest that increased apoptosis may be a central mechanism for accelerated aging. The finding that increased mutations in mtDNA result in aging phenotypes in D257A mice can be readily correlated with normal aging, since mtDNA mutations clearly accumulate to high levels during aging (Y. Wang, et al., supra, 2001; S. Melov, et al., supra, 1997; M. Corral-Debrinksi, et al., supra, 1992; C. M. Lee, et al., supra, 1993; M. Khaidakov, et al., supra, 2003). Surprisingly, our findings do not support one of the major tenets of the free radical hypothesis of aging because accumulation of mtDNA mutations in D257A animals does not lead to increased oxidative stress in either isolated mitochondria or tissues. Because of the stochastic nature of mtDNA mutation accumulation, it is possible that there is a wide distribution of mtDNA mutational load in cells of any given tissue, and that the cells most affected do produce increased ROS levels. However, the observed decrease in hydrogen peroxide production in isolated mitochondria from the heart of D257A mice suggests that reduced mitochondrial function associated with increased mtDNA mutations leads to an overall reduction in mitochondrial ROS production. Possibly, this observation reflects adaptive alterations in mitochondria in the context of an increasing mtDNA mutational load.

If mtDNA mutations contribute to age-related tissue dysfunction, what mitochondrial adaptations contributed to the evolution of long-lived animals? Because cells contain a mixture of wild-type and mutant mtDNAs (heteroplasmy), mtDNA mutations are likely to need to reach a critical threshold prior to cellular dysfunction and apoptosis. It is likely that long-lived organisms evolved mechanisms to minimize the mtDNA mutational load and its consequences because the rate of accumulation of mitochondrial mutations is much faster in mice as compared to humans (E. Wang, et al., *Mutat. Res.* 377:157–166, 1997). Because POLG is a highly conserved enzyme, it appears unlikely that differences in the fidelity of mtDNA replication account for the different rates of accumulation of mtDNA mutations in various organisms. Possibly, the mtDNA mutational load and its consequences are regulated at multiple levels, including mtDNA repair pathways, ROS production and the elimination of dysfunctional mitochondria. Adaptations that increase the mitochondrial apoptotic threshold, such as increased ROS detoxification or modulation of the p53 and p66shc (F. Orsini, et al., *J. Biol. Chem.* 279:25689–25695, 2004) mediated mitochondrial apoptotic pathways, may also have an impact on lifespan in mammals in part by suppressing the effects of mtDNA mutations. In humans, several genetic disorders associated with mitochondrial mutations have been described which are often associated with severe age-related functional decline in tissues with high metabolic demands, including skeletal muscle and brain (D. C. Wallace, *Science* 283:1482–1488, 1999). Mutations of POLG in humans lead to a complex multisystem disorder that can be associated with progressive ophtalmoplegia, sensorimotor polyneuropathy, ataxia, parkinsonism and early menopause (P. Luoma, et al., *Lancet* 364, 875–882, 2004; M. Filosto, et al., *Arch. Neurol.* 60:1279–1284, 2003; M. Mancuso, et al., *Neurology* 62:316–318, 2004). The most severe POLG mutations are dominant and result in alterations in the DNA polymerase domain, resulting in reduced DNA polymerase activity and a 2- to 35-fold decrease in nucleotide selectivity in vitro (M. A. Graziewicz, et al., *Nat. Struct. Mol. Biol.* 11:770–776, 2004). Mutations in the exonuclease domain of POLG have also been reported in humans (M. Filosto, et al., supra, 2003), and these are associated with reduced DNA replication fidelity in vitro and accumulation of point mutations in vivo (R. Del Bo, et al., *Neurology* 61:903–908, 2003). Therefore, similar to our observations in D257A mice, it is likely that accumulation of sporadic mtDNA mutations in humans contributes to the physiological decline associated with aging.

A definitive evaluation of the impact of mtDNA mutations to normal aging in specific species will require the generation of organisms that are engineered to have reduced mtDNA mutation rates (G. M. Martin and L. A. Loeb, *Nature* 429:357–359, 2004). Based on our observations, we hypothesize that mtDNA mutations result in increased apoptosis, leading to functional decline in postmitotic tissues and depletion of stem cell renewal capacity in tissues that display rapid cell turnover. In agreement with this hypothesis, caloric restriction, the only nutritional intervention that retards aging, retards the accumulation of mtDNA mutations in primates and rodents (E. Bua, et al., *FASEB J.* 18:582–584, 2004; L. E. Aspnes, et al., *FASEB J.* 11:573–581, 1997), and reduces mitochondria-mediated apoptotic pathways (H. Y. Cohen, et al., *Science* 305: 390–392, 2004). The availability of mitochondrial mutator mice should allow for the identification of genetic, nutritional and pharmacological interventions that reduce the impact of mtDNA mutations in mammalian aging.

Materials and Methods

Generation of D257A mice.

We used a human cDNA fragment (kindly provided by Dr. W. Copeland) encoding the conserved exonuclease domain region of POLG to screen a λFIXII mouse 129Sv genomic library (Stratagene). We identified two positive clones that hybridized to the cDNA. DNA restriction enzyme mapping was performed on both clones, which demonstrated that they correspond to overlapping regions in the mouse genome. One clone, λGK-1 was used for further characterization. We sequenced the entire 12.3 Kb insert and found that it encoded exons 1 through 18 (FIG. 9). This particular genomic fragment contained sequences encoding all three conserved exonuclease domains of POLG: ExoI, ExoII and ExoIII. We constructed a targeting vector containing two arms of homologous DNA, approximately 5 Kb each. On the 5' targeting vector arm we introduced an AC to CT double base substitution at positions 1054–55 of the mouse PolgA mRNA using a PCR based site-directed mutagenesis strategy. The entire fragment used in this strategy was sequenced to confirm that there were no additional base substitutions introduced by the PCR strategy. The substitution changes the coding of residue 257 from aspartic acid (D) to alanine (A), and introduces in the process a XhoI restriction enzyme site at this position. As a selectable marker for gene targeting, we used a phosphoglycerate kinase promoter-driven neomycin phosphotransferase (neo) gene. Insertion of the neo cassette is designed to occur within intronic DNA (see FIG. 9). We named this allele PolgA$^{D257Aneo}$. We also flanked this neo cassette with Cre recombinase recognition (loxP) sites, which were used for Cre recombinase-mediated excision of the flanked neo cassette in vivo (see below). We named the excised allele PolgA$^{D257A}$.

Once constructed, the targeting vector was linearized and introduced into 129Sv AB2.2 ES cells (a gift from Dr. A.

Bradley). Four hundred two neomycin-resistant ES cell clones were expanded and frozen into 96-well plates. Southern analysis (FIG. S1) of these clones using a 3' probe identified a targeting frequency of ~11% (43 positives out of 402 clones screened). The Southern assay involves detection of an 11.5 Kb targeted allele, as compared to a 15.6 Kb wild-type fragment in a ClaI/NsiI double digest of genomic DNA (FIG. 9). We next performed a PCR assay across the relevant exon 3 region to determine which targeted clones had acquired the desired AC to CT double base substitution at positions 1054–55. PCR with the chosen primers results in an 857 bp product which contains no XhoI sites in wild-type PolgA, but which contains one XhoI site in the PolgA$^{D257Aneo}$ allele. We determined that 95% (40 out of 42) of ES cell clones contained the desired double-base substitution as determined by digestion of PCR products with XhoI, followed by agarose gel electrophoresis.

We next expanded seven correctly targeted ES cell clones and injected these cells into blastocysts derived from C57Bl/6J (B6) female mice. Injected blastocysts were implanted in pseudo-pregnant females for generation of chimeric mice. Eleven chimeric mice were identified as determined by coat color. Of these, five chimeras representing three different ES cell clone lines resulted in germline transmission of the polgA$^{D257Aneo}$ allele when mated to B6 females. Mice carrying one copy of the polgA$^{D257Aneo}$ allele were healthy, fertile, and were used to generate homozygote polgA$^{D257Aneo/D257Aneo}$ mice.

We performed POLG western analysis in heart, skeletal muscle and cell lines derived from polgA$^{D257Aneo}$ mice and determined that POLG protein is expressed in both heterozygous and homozygous polgA$^{D257Aneo}$ mice, suggesting that neither the neo cassette introduced at the PolgA gene, nor the polgA$^{D257A}$ double base-substitution impairs transcription or translation of the PolgA gene. Indeed, expression of the PolgA$^{D257Aneo}$ allele was confirmed by allele specific RT-PCR (data not shown). Heterozygous polgA$^{D257Aneo}$ mice were also crossed to the mixed 129/ICR background Cre recombinase-expressing strain TgN(CMV-Cre)1AN (A. Nagy et al., Curr. Biol. 8:661–664, 1998). Cre is driven from a CMV promoter in this strain, which has been used previously to remove selectable markers flanked by loxP sites (A. Nagy et al., supra, 1998). Excision of the neo cassette, as determined by PCR of genomic DNA, was observed in all tissues tested (brain, heart, kidney, liver, spleen, tail). Additionally, these animals transmitted the rearranged (neo excised) PolgA$^{D257A}$ locus to their offspring. These animals differ from wild-type animals at the PolgA locus by the specific two-base pair alteration introduced in positions 1054–1055 and by a small region (171 bp) containing a loxP site left after the Cre-mediated recombination. Mixed background 129Sv/ICR polgA$^{D257Aneo/+}$ mice were crossed with B6 mice through up to four backcross generations.

Generation and Analysis of Mouse Embryonic Fibroblasts (MEFs).

Females were mated and checked daily for mucous plugs. Animals were sacrificed at 12.5 dpc and embryos isolated from the uterus. Heads were removed for DNA isolation and genotyping. Embryo bodies were minced using sterile scissors and placed in 3 mL syringes with 1 mL of trypsin. The material was passed through an 18-inch gauge needle and incubated for 10 minutes at 37° C. Following trypsin inactivation, the embryonic mixture was transferred into a 6 cm dish. After 24–48 hours, cells were transferred to a 10 cm dish. Cells were frozen upon confluence as passage 1.

For studies of replicative senescence, cultures were passaged using a 1:4 subculture regimen and incubated at 37° C. in a hypoxic atmosphere of 93% $N_2$, 5% $CO_2$, and 2% $O_2$ or normoxic atmosphere of 75% $N_2$, 5% $CO_2$, and 20% $O_2$. Cells were cultured in Ham's F10 nutrient mixture (Life Technologies) supplemented with 10% fetal bovine serum (Hyclone), 20 mM L-glutamine (Gibco BRL), and penicillin/streptomycin (Gibco BRL).

Sequencing of mtDNA.

Mitochondria were isolated from heart, duodenum and liver from individual animals (2/group, 5–6 months of age) by differential centrifugation as previously described (Y. Hatefi, Methods Enzymol. 53:48–54, 1978). For sperm analysis, sperm was isolated by incubating sliced cauda epididymis in PBS at 37° C. for 30 minutes followed by removal of the cauda and sperm pelleting by centrifugation. DNA was isolated by overnight digestion with 0.5 mg/ml proteinase K in TENS buffer (50 mM Tris, pH 8.0; 100 mM EDTA; 200 mM NaCl; 1% SDS), followed by ethanol precipitation. DNA preparations were digested with DraIII and BglII followed by treatment with Exonuclease III in order to degrade any contaminating nuclear DNA. A mitochondrial DNA fragment of 525 bp was amplified by PCR (MTC1 primer, gCCAACTAgCCTCCATCTCATACTT, nt 15196–15220 in B6 mtDNA, SEQ ID NO: 4; MTC2 primer, gggCgggTTgTTggTTTCAC, nt 15701–15720, SEQ ID NO: 5) using Easy-A Hi-Fidelity™ cloning enzyme (Stratagene). PCR products were cloned into pCR4-TOPO™ vector using TOPO™ TA Cloning Kit (Invitrogen). One hundred ninety-two colonies of each individual tissue source were grown and plasmid DNA isolated using the QIAPREP TURBO 96 Mini-prep Kit (Qiagen). Plasmid DNA was sequenced using standard M13 forward and reverse primers. Reaction products were purified using Clean-seq magnetic beads (Agencourt) and sequenced on an ABI 3730xl capillary sequencer. DNA sequences were aligned to the B6 mtDNA reference sequence (Accession: NC_005089) using Aligner software (CodonCode™) for identification of mutations. Each tissue source yielded approximately 180,000 bases of sequence, totaling over 300,000 bases per tissue per genotype for the two pair analysis.

Histological Procedures.

Tissues and organs were collected from mice following sacrifice according to a standard necropsy protocol. The entire thymus was fixed in 10% buffered formalin solution, as were both testes. A segment of each duodenum and small intestine, 3.5 cm long beginning at the pylorus, was opened longitudinally, pinned to a paper card, and fixed for at least 24 hours. Before further processing, the intestine was rolled into a spiral and pinned in position. Each testis was sliced longitudinally into two equal pieces following fixation. Fixed tissues were processed through a series of ethanol solutions of increasing concentrations, cleared in xylene, and embedded in paraffin. Prior to the final step of embedment, the rolled intestines were sliced into two halves, representing a division of the intestine into two longitudinal pieces. The two halves were embedded together so that subsequent sections were mirror images. Sections of all tissues were cut at 5 μm and two slices were mounted on Fisher Superfrost Plus slides.

For histopathology of inner ear, mice were decapitated under deep anesthesia with 240 mg/kg tribromoethanol. After removing the temporal bones, the cochleae were perfused with 2% paraformaldehyde and 2.5% glutaraldehyde in phosphate buffered saline (PBS) through the round and oval windows, immersed in the same fixative for 24 hours, and decalcified in 10% EDTA (pH 7.2) for 24 hours. The cochleae were then rinsed with PBS, dehydrated through a graded series of alcohol, and embedded in epoxy resin. Thin sections cut parallel to the modiolus were stained with 0.5% toluidine blue and were observed under a light microscope.

TUNEL Staining.

Paraffin was removed from the sections with xylene followed by ethanol and rinsed in water. TUNEL staining for apoptotic nuclei was performed using the DeadEnd™ Colormetric TUNEL System (Promega, Madison) according to the manufacturer's instructions. Following preliminary studies, permeabilization with proteinase K was omitted as unnecessary for staining in these tissues. Labeling reactions were performed for 60 minutes at 25° C. in a humidified chamber. Color development was accomplished with DAB for 8 minutes. Duplicate sections were counter-stained with hematoxylin and all slides were covered with a coverglass mounted with Permount.

Sections were examined with a Leica DM LB microscope using a 40× objective. Positively-stained apoptotic nuclei were counted in sections of intestine, thymus, and testes by direct observation. For sections of intestine, the entire length represented in the sections were viewed and counted. The number of villi represented in the length were counted under the 10× objective. Apoptosis was evaluated as the number of positively-stained nuclei per 100 villi. Sections of thymus were sampled by random movement of the mechanical microscope stage to bring new, non-overlapping areas into view. Five fields of 300 μm×225 μm, as seen using the 40× objective, were sampled for each thymus (total=0.36 mm$^2$). Counts were standardized from the mean number of apoptotic-positive cells per field to number per $1\times10^5$ μm$^2$. Apoptotic nuclei in testes were counted in a representative longitudinal cross-section of one testis from each mouse. The number of cross-sections of tubules for each sample was determined from counts on low magnification mosaic photos of each testis. The number of apoptotic nuclei per cross-section of seminiferous tubule was calculated for each mouse.

Assessment of Hearing Function.

Hearing function was tested in 2 month old and 9 month old wild-type and D257A mice. Auditory brainstem responses (ABRs) were measured with a tone burst stimulus (4, 8, and 16 kHz) using an ABR recording system (Intelligent Hearing System, Miami, Fla.). Animals were anesthetized with a mixture of xylazine hydrochloride (10 mg/kg, i.m.) and ketamine hydrochloride (40 mg/kg, i.m.), and needle electrodes were placed subcutaneously at the vertex (active electrode), beneath the pinna of the measured ear (reference electrode), and beneath the opposite ear (ground). The stimulus duration, presentation rate, and rise/fall time were 3 ms, 19.3/s, and 1 ms respectively. Responses of 1024 sweeps were averaged at each intensity level (5 dB steps) to assess threshold. Threshold was defined as the lowest intensity level at which a clear reproducible waveform was visible in the trace. Five mice per genotype at each age were used for the study.

Measurement of Heart Function.

Transthoracic echocardiography was performed using *an Acuson Sequoia* (Siemens) ultrasonograph with a 15-MHz transducer. For acquisition of two-dimensional guided M-mode images at the tips of papillary muscles and Doppler studies, mice were sedated by IP administration of 100 mg/kg ketamine and maintained on a heated platform in a left lateral decubitus position. The chest was shaved and prewarmed coupling gel applied. Transmitral velocities were measured using Doppler pulse wave imaging. All images were saved to an on-board optical disk.

End diastolic and systolic left ventricular (LV) diameter as well as anterior and posterior wall (AW and PW respectively) thicknesses were measured on line from M-mode images using the leading edge-to-leading edge convention. All parameters were measured over at least three consecutive cardiac cycles and averaged. Left ventricular fractional shortening was calculated as [(LV diameter$_{diastole}$−LV diameter$_{systole}$)/LV diameter$_{diastole}$]×100 and LV mass was calculated by using the formula [1.05×((Posterior Wall$_{diastole}$+Anterior Wall$_{diastole}$+LV diameter$_{diastole}$)$^3$−(LV diameter$_{diastole}$)$^3$)]. Relative wall thickness was calculated as 2×Posterior wall$_{diastole}$/LV diameter$_{diastole}$. Heart rate was determined from at least three consecutive intervals from the pulse wave Doppler tracings of the LV outflow tract. Isovolumic relaxation time was measured as the time from the closing of the aortic value to the opening of the mitral value from pulse wave Doppler tracings of the LV outflow tract and mitral inflow region. The same person obtained all images and measures.

Measurement of DNA and RNA Oxidation Markers.

Liver nuclei-pellets were dissolved in 3M guanidine isothiocyanate, 0.2% sodium N-lauroylsarcosinate, 20 mM Tris, pH 7.5 containing 10 mM freshly dissolved deferoxamine mesylate by pipetting on ice. Fat and proteins were removed by extraction with phenol/chloroform/isoamylalcohol (25:24:1). The aqueous phase was withdrawn and after chloroform/isoamylalcohol (24:1) extraction to remove traces of phenol, nucleic acids were precipitated by addition of isopropanol (−80° C., 1 h). After washing in 70% ethanol, nucleic acids pellets were dissolved in water containing 30 μM deferoxamine mesylate and hydrolysed using nuclease P$_1$ and alkaline phosphatase. Nucleoside content of guanosine (RNA), 8-hydroxyguanosine (RNA), 2'-deoxyguanosine (DNA) and 8-hydroxy-2'-deoxyguanosine (DNA) was determined using HPLC-EC-UV (T. Hofer and L. Moller, *Chem. Res. Toxicol.* 15:426–432, 2002).

Mitochondrial and Cytosolic Extracts.

Animals were sacrificed at 3 months and 9 months of age. Animals were anesthetized with isoflurane gas, which was administered via inhalation using a precision vaporizer at 3%. Following anesthesia the chest cavity was opened and the heart was removed rapidly, followed by liver, thymus, testes, duodenum, skeletal muscle, and inner ear tissue. Mitochondrial and cytosolic protein fractions were isolated using differential centrifugation. Briefly, heart and liver were finely minced and homogenized on ice in 1:10 (wt/vol) ice-cold isolation buffer (heart buffer composition: 220 mM mannitol, 70 mM sucrose, 1 mM EDTA, and 10 mM Tris-HCl, 0.2% fatty acid free BSA, pH 7.4; liver buffer composition: 210 mM mannitol, 70 mM sucrose, 1 mM EDTA, 5 mM HEPES, pH 7.35) using a POTTER-ELVEHJEM glass homogenizer. The homogenates from heart and liver were centrifuged for 10 minutes at 700 g and 1000 g, respectively, and the resulting supernatants were centrifuged for 20 minutes at 8,000 g (heart) or 10,000 g (liver). The 8,000 g and 10,000 g supernatants (representing crude cytosolic fractions) were frozen at −80° C. for analysis. Pellets were resuspended in a small volume of isolation buffer and centrifuged at 8,000 g (heart) or 10,000 g (liver) for 10 minutes. All centrifugation steps were carried out at 4° C. The final mitochondrial pellets were suspended in isolation buffer (without BSA, for heart mitochondria and without EDTA, for liver mitochondria) and used immediately for measurement of mitochondrial $H_2O_2$ and ATP production. For cytosolic extraction from thymus, duodenum, testes and gastrocnemius muscle, tissues were homogenized in 1:10 (wt/vol) (1:5 for skeletal muscle) ice-cold isolation buffer (20 mM HEPES, 10 mM KCl, 250 mM sucrose, 1.5 mM $MgCl_2$, 1 mM EDTA, pH 7.4). The homogenates were centrifuged at 800–1000 g depending on the tissue for 10 minutes, and the resulting supernatants were centrifuged at 10,000 g for 20 minutes. The supernatants (crude cytosol) were immediately frozen at −80° C. for further biochemical analysis.

Determination of Cytosolic Mono- and Oligonucleosomes.

Endogenous endonucleases activated during apoptosis cleave double-stranded DNA in the linker region between nucleosomes to generate mono- and oligonucleosomes of 180 bp or multiples. Apoptotic DNA fragmentation was quantified in the thymus and testes by measuring the amount of cytosolic mono- and oligonucleosomes using a Cell Death™ ELISA kit (ROCHE MOLECULAR BIOCHEMICALS, Germany) with the peroxidase substrate ABTS (A. Dirks and C. Leeuwenburgh, *Am. J. Physiol. Regul. Integr. Comp. Physiol.* 282:R519–R527, 2002; S. K. Lee, et al., *Anticancer Res.* 22:97–102, 2002). All samples were run in triplicate and the means expressed as arbitrary OD units normalized to milligram of cytosolic protein, with sample protein concentrations determined by the Bradford method (M. M. Bradford, *Analyt. Biochem.* 72:248–254, 1976).

Determination of Cleaved Caspase-3 Content.

The active form of caspase-3, cleaved caspase-3, was quantified by Western blotting. Activation of caspase-3 requires proteolytic processing of its inactive zymogen into activated fragments. The specific antibody used (see below) detects endogenous levels of the large fragment (17/19 kDa) of activated caspase-3 resulting from cleavage adjacent to Asp175. For quantification of cleaved caspase-3 by Western blot analysis, cytosolic proteins from the thymus, testes, duodenum and gastrocnemius muscle were separated using 4–20% PAGEr® Gold pre-cast Tris-glycine gels (BioWittaker Molecular Applications, Rockland, Me., USA) under denaturing conditions, and then transferred to nitrocellulose membranes (0.2 μm, Trans-Blot® Transfer Medium, Bio-Rad Laboratories, California, USA). Protein concentration was determined using the Bradford assay (M. M. Bradford, supra, 1976), and subsequently normalized so that the protein content among samples was identical. Subsequently, 20 μl of sample was loaded to each well. A 15 μl sample of HL-60 cell extract induced with etoposide (EMD Biosciences, Inc., San Diego, Calif.) was used as a positive control. Only protein bands within an individual gel were used for comparisons. Membranes were blocked for 1 h using a blocking solution containing PBS and 5% milk. Membranes were then incubated overnight in the 5% blocking solution containing the rabbit monoclonal primary anti-cleaved caspase-3 antibody (Cell Signaling, Beverly, Mass., USA) with an appropriate dilution (1:100 for gastrocnemius and testes, 1:300 for thymus, and 1:1000 for duodenum). The following day membranes were incubated for 1 hour at room temperature with anti-rabbit IgG horseradish peroxidase-linked whole secondary antibody (1:1000, Amersham Biosciences UK Ltd, Amersham, UK). Specific protein bands were visualized using ECL reagent (Amersham Pharmacia Biotech, UK). The resulting Western blots were exposed to film (Hyperfilm™ ECl™, Amersham Pharmacia Biotech, UK) and analyzed using the KODAK Imaging System (Kodak 440CF). Values were expressed as arbitrary OD units. Triplicate measurements were taken and the resulting means (±SEM) were used for analysis.

Oxidant Production.

$H_2O_2$ production was measured in intact heart and liver mitochondria over a period of 15 minutes at 37° C. following the method of Barja (G. Barja, *J. Bioenerg. Biomembr.* 34:227–233, 2002). Briefly, incubation buffer (145 mM KCl, 30 mM HEPES, 5 mM $KH_2PO_4$, 3 mM $MgCl_2$, 0.1 mM EGTA, and 0.1% fatty-acid free BSA, pH 7.4) was added to test tubes followed by the addition of mitochondria (0.25 mg protein/ml), horseradish peroxidase (5.7 U/ml), homovanilic acid (0.1 mM), and substrate (2.5 mM pyruvate/malate) so that the total volume was equal to 1.5 ml. The tubes were incubated in a shaking water bath at 37° C. for 15 minutes, and the reaction was stopped by placing the tubes in ice and adding 0.5 ml cold stop solution (0.1 M glycine, 25 mM EDTA-NaOH, pH 12.0). Fluorescence was determined at 312 nm excitation and 420 nm Emission using a SPECTRAmax Gemini™ XS dual-scanning microplate spectrofluorometer (Molecular Devices, Sunnyvale, Calif.). Arbitrary fluorescence units were converted to known amounts of $H_2O_2$ using a glucose—glucose oxidase standard curve. All measurements were performed in duplicate, and results were expressed as nmol of $H_2O_2$/min/mg protein.

ATP Production.

Mitochondria isolated from heart and liver were used immediately after isolation to determine mitochondrial ATP content and rate of ATP production following the method of Drew (B. Drew and C. Leeuwenburgh, *Am. J. Physiol. Regul. Integr. Comp. Physiol.* 285:R1259–R1267, 2003). ATP production was determined using a luminometer (model TD-20/20, Turner Designs, Sunnyvale, Calif.), employing an assay that utilizes firefly luciferase, which fluoresces in proportion to the presence of ATP and d-luciferin. In order to determine ATP content, freshly isolated mitochondria were added to a cuvette containing 1 mM pyruvate, 1 mM malate, and a luciferin-luciferase ATP monitoring reagent (ATP Determination Kit A-22066, Molecular Probes, Eugene, Oreg.). This was followed immediately by the addition of 2.5 mM ADP to determine ATP production. A blank cuvette containing no sample was assayed to account for nonspecific ATP production, and known concentrations of ATP were used to establish a standard curve. All mitochondrial samples were assayed in triplicate, and an average of these results was used in quantifying ATP content and rate of production. Results (mean±SEM) for ATP content were expressed as nmol ATP/mg protein, and for ATP production as nmol ATP/mg protein/min.

Statistical Analysis.

All analyses were performed in triplicate and the means obtained were used for independent t-tests. Statistical analyses were carried out using the Prism 4.0 statistical analysis program (GraphPad, San Diego Calif.). Statistical significance was set at $P<0.05$. All data are reported as mean±SEM.

Those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims below.

We claim:

1. A transgenic mouse model for mouse aging comprising a mouse having a targeted site-directed mutation in the exonuclease domain II of the endogenous mitochondrial DNA polymerase gamma gene, wherein said targeted site-directed mutation is the substitution of an aspartic acid residue to an alanine residue at position 257 as set forth in SEQ ID NO:3, wherein said mutation results in an elevated mitochondrial mutation frequency in at least two tissues in said mouse model.

2. The mouse model of claim 1 wherein the exonuclease domain mutation results in the expression of a DNA proofreading deficient version of the mitochondrial DNA polymerase gamma (Polg) gene and accumulation of mitochondrial DNA mutations in both mitotic and post-mitotic mouse tissues, which is correlated with the activation of caspase-3 and the induction of apoptosis in mouse tissues.

3. The mouse model of claim 1 wherein the mouse exhibits symptoms of accelerated or premature aging compared to a mouse not having the mutation in the exonuclease domain of the Polg gene.

4. The mouse model of claim 1 wherein the aging symptoms are selected from the group consisting of abnormalities in tissues of high cellular turnover, heart dysfunction, graying hair and alopecia, auditory function loss, cochlear degeneration, immune cell loss, anemia, male germ cell loss leading to lack of sperm and infertility, skeletal muscle mass loss neurodegeneration, increased presence of apoptotic markers, and loss of bone mass.

5. A method of screening for a potentially therapeutic agent useful for delaying the onset of aging-related symptoms, the method comprising the steps of:
 (a) providing a mouse model of claim 1, wherein the mouse exhibits aging-related symptoms;
 (b) administering the agent to the mouse model; and
 (c) determining whether the agent is capable of delaying the onset of aging-related symptoms in the mouse model treated with the agent compared to an untreated mouse model.

6. The method of claim 5 wherein the aging-related symptoms are selected from the group consisting of abnormalities in tissues of high cellular turnover, heart dysfunction, graying hair and alopecia, auditory function loss, cochlear degeneration, immune cell loss, anemia, male germ cell loss leading to lack of sperm and infertility, skeletal muscle mass loss, bone loss, neurodegeneration and increased presence of apoptotic stress markers.

7. The method of claim 5 wherein the age-related symptoms are selected from the group consisting of altered hearing function, altered heart function, loss of bone, loss of muscle mass and induction of apoptosis.

8. The method of claim 5 wherein the therapeutic agent is a genetically-, a pharmaceutical- or a dietary-based agent.

9. A method of screening for a potentially therapeutic agent useful for treating medical conditions comprising progressive external ophthalmoplegia, sensorimotor polyneuropathy, ataxia, Parkinson's syndrome or early menopause defined by mitochondrial DNA mutations in a POLG gene, the method comprising the steps of:
 (a) providing a mouse model of claim 1, wherein the mouse exhibits symptoms of progressive external ophthalmoplegia sensorimotor polyneuropathy, ataxia, Parkinson's syndrome or early menopause;
 (b) administering the agent to the mouse model; and
 (c) determining whether the agent is capable of improving symptoms for any of the medical conditions of step (a) in the mouse model treated with the agent compared to an untreated mouse model.

* * * * *